US012564840B2

(12) United States Patent
van Dam et al.

(10) Patent No.: US 12,564,840 B2
(45) Date of Patent: Mar. 3, 2026

(54) HIGH THROUGHPUT RADIOCHEMISTRY SYSTEM

(71) Applicant: THE REGENTS OF THE UNIVERSITY OF CALIFORNIA, Oakland, CA (US)

(72) Inventors: R. Michael van Dam, Los Angeles, CA (US); Jia Wang, Los Angeles, CA (US); Alejandra Rios, Los Angeles, CA (US); Philip Chao, Los Angeles, CA (US); Jason Jones, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1069 days.

(21) Appl. No.: 17/622,206

(22) PCT Filed: Aug. 7, 2020

(86) PCT No.: PCT/US2020/045378
§ 371 (c)(1),
(2) Date: Dec. 22, 2021

(87) PCT Pub. No.: WO2021/026441
PCT Pub. Date: Feb. 11, 2021

(65) Prior Publication Data
US 2022/0401960 A1     Dec. 22, 2022

Related U.S. Application Data

(60) Provisional application No. 62/884,352, filed on Aug. 8, 2019.

(51) Int. Cl.
*B01L 7/00*          (2006.01)
*B01L 3/00*          (2006.01)
(Continued)

(52) U.S. Cl.
CPC ............... B01L 7/00 (2013.01); B01L 3/5085 (2013.01); G01N 35/0099 (2013.01);
(Continued)

(58) Field of Classification Search
CPC ............... B01L 7/52; B01L 9/527; B01L 9/52
See application file for complete search history.

(56) References Cited

U.S. PATENT DOCUMENTS 4,865,986 A * 9/1989 Coy ......................... F25B 21/02
                                                        422/63
5,616,301 A * 4/1997 Moser ....................... B01L 7/52
                                                        422/562
(Continued)

FOREIGN PATENT DOCUMENTS

CN          107377023          11/2017
WO          2007/041486          4/2007
(Continued)

OTHER PUBLICATIONS

PCT International Search Report for PCT/US2020/045378, Applicant: The Regents of the University of California, Form PCT/ISA/210 and 220, dated Nov. 6, 2020 (4 pages).
(Continued)

*Primary Examiner* — Natalia Levkovich
(74) *Attorney, Agent, or Firm* — VISTA IP LAW GROUP LLP

(57) ABSTRACT
A radiosynthesis system is disclosed that leverages droplet microfluidic radiosynthesis and its inherent advantages including reduction of reagent consumption and the ability to achieve high molar activity even when using low starting radioactivity. The radiosynthesis system enables the parallel synthesis of radiolabeled compounds using droplet-sized reaction volumes. In some embodiments, a single heater is used to create multiple reaction or synthesis sites. In other
(Continued)

embodiments, separate heaters are used to create independently-controlled heating conditions at the multiple reaction or synthesis sites. In one embodiment, a four-heater setup was developed that utilizes a multi-reaction microfluidic chip and was assessed for the suitability with high-throughput radiosynthesis optimization. Replicates of several radiochemical operations including the full synthesis of various PET tracers revealed the platform to have high repeatability (e.g., consistent fluorination efficiency). The system may also be used for synthesis optimization.

15 Claims, 19 Drawing Sheets

(51) Int. Cl.

| | | |
|---|---|---|
| *G01N 35/00* | (2006.01) | |
| *G01N 30/02* | (2006.01) | |
| *G01N 33/00* | (2006.01) | |

(52) U.S. Cl.

CPC ................. *B01L 2300/0663* (2013.01); *B01L 2300/0829* (2013.01); *B01L 2300/165* (2013.01); *G01N 2030/027* (2013.01); *G01N 33/0093* (2024.05); *G01N 2035/00376* (2013.01); *G01N 2035/00445* (2013.01)

(56) References Cited

U.S. PATENT DOCUMENTS

| | | | |
|---|---|---|---|
| 6,485,690 | B1 | 11/2002 | Pfost et al. |
| 7,829,032 | B2 | 11/2010 | van Dam et al. |
| 8,071,035 | B2 | 12/2011 | Elizarov et al. |
| 8,075,851 | B2 | 12/2011 | Elizarov et al. |
| 8,173,073 | B2 | 5/2012 | Elizarov et al. |
| 8,658,112 | B2 | 2/2014 | Elizarov et al. |
| 8,951,480 | B2 | 2/2015 | Satyamurthy et al. |
| 9,005,544 | B2 | 4/2015 | van Dam et al. |
| 9,193,640 | B2 | 11/2015 | van Dam et al. |
| 9,211,520 | B2 | 12/2015 | Satyamurthy et al. |
| 9,481,615 | B2 | 11/2016 | van Dam et al. |
| 9,481,705 | B2 | 11/2016 | Satyamurthy et al. |
| 9,649,632 | B2 | 5/2017 | van Dam et al. |
| 10,081,005 | B2 | 9/2018 | Moore et al. |
| 10,473,668 | B2 | 11/2019 | van Dam et al. |
| 10,589,250 | B2 | 3/2020 | Schopf et al. |
| 2008/0131327 | A1 | 6/2008 | van Dam et al. |
| 2008/0233018 | A1 | 9/2008 | van Dam et al. |
| 2009/0036668 | A1 | 2/2009 | Elizarov et al. |
| 2009/0095635 | A1 | 4/2009 | Elizarov et al. |
| 2011/0097245 | A1 | 4/2011 | Elizarov et al. |
| 2012/0101268 | A1 | 4/2012 | Elizarov et al. |
| 2012/0107175 | A1 | 5/2012 | Satyamurthy et al. |
| 2012/0264932 | A1 | 10/2012 | van Dam et al. |
| 2015/0148549 | A1 | 5/2015 | van Dam et al. |
| 2015/0203416 | A1 | 7/2015 | van Dam et al. |
| 2015/0238918 | A1 | 8/2015 | Khachaturian et al. |
| 2015/0329583 | A1 | 11/2015 | Satyamurthy et al. |
| 2016/0107951 | A1 | 4/2016 | van Dam et al. |
| 2016/0130295 | A1 | 5/2016 | Satyamurthy et al. |
| 2016/0280734 | A1 | 9/2016 | Moore et al. |
| 2016/0298173 | A1 | 10/2016 | Wang et al. |
| 2017/0102391 | A1 | 4/2017 | van Dam et al. |
| 2018/0065103 | A1 | 3/2018 | Schopf et al. |
| 2019/0201560 | A1 | 7/2019 | Chao et al. |
| 2020/0147548 | A1 | 5/2020 | van Dam et al. |
| 2020/0179927 | A1 | 6/2020 | Wang et al. |

FOREIGN PATENT DOCUMENTS

| | | |
|---|---|---|
| WO | 2008/091694 | 7/2008 |
| WO | 2008/128201 | 10/2008 |
| WO | 2009/015048 | 1/2009 |
| WO | 2010/021719 | 2/2010 |
| WO | 2011/046615 | 4/2011 |
| WO | 2013/185142 | 12/2013 |
| WO | 2014/160799 | 10/2014 |
| WO | 2015/188165 | 12/2015 |
| WO | 2018/048856 | 3/2018 |
| WO | 2018/048873 | 3/2018 |
| WO | 2018/067965 | 4/2018 |
| WO | 2018/093794 | 5/2018 |
| WO | 2020/219318 | 10/2020 |
| WO | 2020/237195 | 11/2020 |
| WO | 2021/026441 | 2/2021 |

OTHER PUBLICATIONS

PCT Written Opinion of the International Search Authority for PCT/US2020/045378, Applicant: The Regents of the University of California, Form PCT/ISA/237, dated Nov. 6, 2020 (7 pages).

Philip H. Chaoa et al., Automated concentration of [18F]fluoride into microliter volumes, Applied Radiation and Isotopes 141 (2018) 138-148.

Alex A. Dooraghia et al., Optimization of microfluidic PET tracer synthesis with Cerenkov imaging†, Analyst. Oct. 7, 2013; 138(19): 5654-5664.

Pei Yuin Keng et al., Advantages of Radiochemistry in Microliter Volumes, Perspectives on Nuclear Medicine for Molecular Diagnosis and Integrated Therapy, DOI 10.1007/978-4-431-55894-1_7 (2016).

Pei Yuin Keng et al., Digital Microfluidics: A New Paradigm for Radiochemistry, Molecular Imaging, vol. 14 (Dec. 2015): pp. 579-594.

S.Y. Lu et al., Micro-reactors for PET Tracer Labeling, pp. 271-287 (2007).

Jimmy Ly et al., Automated Reagent-Dispensing System for Microfluidic Cell Biology Assays, Journal of Laboratory Automation 18(6) 530-541.

Alejandra Rios et al., A novel multi-reaction microdroplet platform for rapid radiochemistry optimization, RSC Adv., 2019, 9, 20370.

Eric Schopf et al., Automation of a Positron-emission Tomography (PET) Radiotracer Synthesis Protocol for Clinical Production, J. Vis. Exp. (140), e58428, doi:10.3791/58428 (2018).

Maxim Sergeev et al., Performing radiosynthesis in microvolumes to maximize molar activity of tracers for positron emission tomography, Communications Chemistry, (2018) 1:10; DOI: 10.1038/s42004-018-0009-z.

Jia Wang et al., Performing multi-step chemical reactions in microliter-sized droplets by leveraging a simple passive transport mechanism, Lab Chip. Dec. 5, 2017; 17(24): 4342-4355.

Jia Wang et al., Ultra-compact, automated microdroplet radiosynthesizer, Lab Chip. Jul. 21, 2019; 19(14): 2415-2424.

Response to the extended European Search Report dated Jul. 20, 2023 for European Patent Application No. 20849946, Applicant: The Regents of the University of California, (66 pages).

PCT International Preliminary Report on Patentability (Chapter I of the Patent Cooperation Treaty) for PCT/US2020/045378, Applicant: The Regents of the University of California, Form PCT/IB/326 and 373, dated Feb. 17, 2022 (9 pages).

The extended European Search Report dated Dec. 23, 2022 for European Patent Application No. 20849946, Applicant: The Regents of the University of California, (9 pages).

Communication pursuant to Rules 70(2) and 70a(2) EPC dated Jan. 11, 2023 for European Patent Application No. 20849946, Applicant: The Regents of the University of California, (1 page).

Johanna Ungersboeck et al., Microfluidic preparation of [18F]FE@SUPPY and [18F]FE@SUPPY:2—comparison with conventional radiosyntheses, Nuclear Medicine and Biology, 38 (2011) 427-434.

* cited by examiner

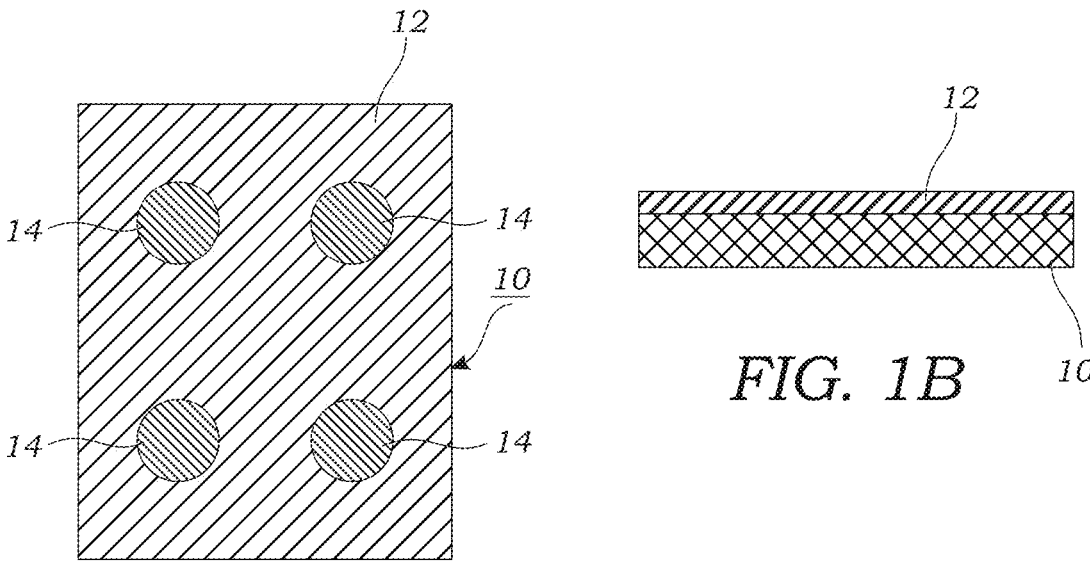
*FIG. 1A*
*FIG. 1B*
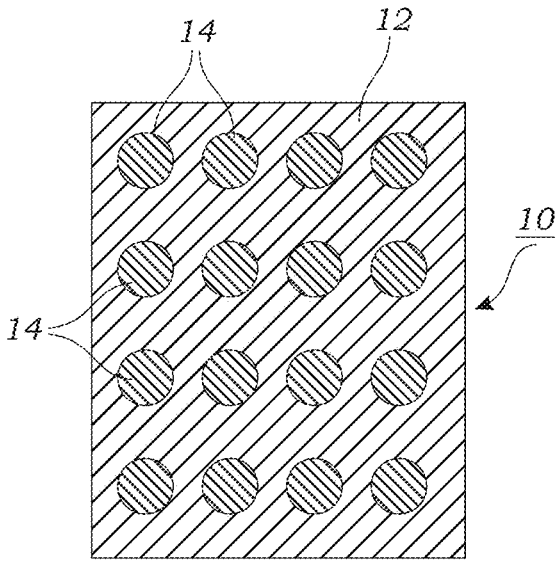
*FIG. 1C*

HIGH THROUGHPUT RADIOCHEMISTRY SYSTEM

RELATED APPLICATION

This Application is a U.S. National Stage filing under 35 U.S.C. § 371 of International Application No. PCT/US2020/045378, filed on Aug. 7, 2020, which claims priority to U.S. Provisional Patent Application No. 62/884,352 filed on Aug. 8, 2019, which are hereby incorporated by reference. Priority is claimed pursuant to 35 U.S.C. §§ 119, 371 and any other applicable statute.

STATEMENT REGARDING FEDERALLY SPONSORED RESEARCH AND DEVELOPMENT

This invention was made with government support under Grant Numbers CA212718 and MH097271, awarded by the National Institutes of Health. The government has certain rights in the invention.

TECHNICAL FIELD

The technical field generally relates to devices and methods that utilize droplet-based synthesis methods and protocols for the synthesis of radiolabeled compounds. The technical field more particularly relates to devices and systems that perform droplet-based synthesis methods in parallel to achieve high throughput.

BACKGROUND

Positron emission tomography (PET) is a real-time, in vivo 3D imaging technique that has unparalleled specificity and sensitivity for visualizing biochemical processes. This technique offers the potential to identify diseases in its earliest stages as well as a patient's immediate response to therapeutic intervention. It is commonly used for cancer research and pharmacokinetic studies. PET works by detecting pairs of gamma rays from a positron-emitting tracer that is introduced into the body. Despite the increasing importance of PET imaging in biological and clinical research, access to myriad new radioactive tracers is limited. This is in part due to the short half-life, which requires daily production close to the site of use, and due to the high complexity of tracer production, which requires costly equipment operated behind radiation shielding and other safety infrastructure.

Though basic research efforts are leading to the discovery of numerous novel biological targets that are suitable therapeutic targets or indicators of response, there is a lag of many years or more in the development of effective PET tracers to visualize these targets in vivo. Approaches such as library screening help to generate sets of candidate tracers that share reaction conditions and/or having similar routes to precursor production; however, the high cost of radiolabeling only allows a tiny fraction of the top-ranking initial candidates to be labeled for detailed evaluation. This leads to a slow, incremental tracer development process, which is further complicated by the fact that results of in vitro assays for selecting the top few candidates are poorly correlated with in vivo tracer performance. For example, using conventional candidate screening methods, the best in vivo performers may be poorly ranked by in vitro methods and normally would be discarded. Conversely, the best in vitro performers may turn out to have very poor in vivo performance. This discordance highlights the need to perform in vivo evaluation of larger libraries earlier in tracer development.

The development of larger libraries of tracers requires the simultaneous radiolabeling of many compounds. However, the problem of simultaneous radiolabeling of many compounds has not yet been solved. Challenges in performing high-throughput reactions with current radiosynthesis methods include the high precursor amounts/costs, the bulky size and high cost of apparatus, and the difficulty in having enough isotope in each reaction to ensure sufficiently high specific activity for imaging. There thus is a need for a single radiosynthesis device and system that can perform simultaneous radiolabeling of multiple compounds.

SUMMARY

In one embodiment, a high throughput chemistry synthesis system is disclosed that enables one to perform large numbers of chemical reactions in parallel. The high throughput chemistry synthesis system utilizes microfluidic components to perform reactions within droplet-sized reaction volumes. The chemistry synthesis system has particular applicability to radiochemistry-based synthesis but is not so limited. In one embodiment, the high throughput chemistry synthesis system includes a microfluidic chip or substrate that has formed thereon a plurality of discrete reaction sites. Each reaction site on the microfluidic chip or substrate may be formed, in one embodiment, as a discrete hydrophilic region that holds droplet(s) therein during the radiolabeling reactions. For example, the microfluidic chip or substrate, which is flat, may contain a hydrophobic coating such as polytetrafluoroethylene or Teflon® with hydrophilic reaction sites formed therein using standard photolithographic methods. Each reaction site is located on the microfluidic chip or substrate so as to not interfere with adjacent droplet(s) at neighboring reaction sites.

In one embodiment, the microfluidic chip or substrate is in thermal contact with a heater platform that contains one or more heaters therein. For example, the microfluidic chip or substrate may be located on top of a heater platform that contains, in one embodiment, a single heater. In other embodiments, the heater platform may include a plurality of heaters with each separate heater being located adjacent to different reaction sites of the microfluidic chip or substrate when loaded onto the heater platform. In other embodiments where multiple microfluidic chips or substrates are run, each microfluidic chip or substrate may be located adjacent to a separate heater in the heater platform. Thus, in some embodiments, each reaction site (or all reaction sites on a single microfluidic chip or substrate) may be located adjacent to its own heater that can be individually controlled. In other embodiments, however, a single heater may be used for multiple reaction sites.

In one aspect, the heater platform may be formed from a ceramic holder with the different heaters potted in the ceramic holder. The heaters may include high-power ceramic heaters (e.g., aluminum nitride) that are controlled independently via the amount of electrical current supplied or through, for example, on-off control of the heaters. The heater platform may also contain one or more cooling devices (e.g., fans) that are used to aid in cooling the microfluidic chip or substrate and/or reaction sites. In one embodiment, each separate reaction site (or microfluidic chip or substrate) may be associated with its own cooling fan although in other embodiments multiple reaction sites (or multiple microfluidic chips or substrates) may be cooled by a single cooling fan. The cooling fans are used to cool the respective reaction sites. In some embodiments, the heater platform and the optional mount or base for the fans may optionally incorporate exhaust vents or other features that direct airflow across a surface of the heater(s) therein to aid in reducing cooling time. Temperature is monitored via sensors such as thermocouples associated with each heater. One or more controllers or control circuitry may be used to independent control the heaters and fans to maintain the desired temperature at each reaction site. The temperature of the microfluidic chip or substrate (or reaction sites contained therein) can be quickly ramped (up or down) by the use of the controllable heaters and fans.

In one particular embodiment, the heater platform may accommodate a plurality of microfluidic chips or substrates with each microfluidic chip or substrate having multiple reaction sites thereon. For example, as one illustrative example, a heater platform may have four (4) separate heaters formed therein and the heater platform may accommodate four (4) different microfluidic chips or substrates each having four (4) reaction sites formed thereon. Of course, the microfluidic chips or substrates may have more or fewer reaction sites. Four separate cooling fans are associated each of the four different heaters. In this example, the platform enables one to perform sixteen (16) reactions simultaneously. It should be appreciated that any number of microfluidic chips or substrates can be loaded onto the heater platform. This may include a single microfluidic chip or substrate (with multiple reaction sites) or multiple microfluidic chips or substrates. The heater platform may include any number of heaters, from a single heater to multiple different heaters (e.g., one heater for each microfluidic chip or substrate).

In one embodiment, a robotic fluid handling system may be provided to load/remove fluid onto and from the microfluidic chip(s) or substrate(s). For example, robotic gantry system having the ability to move in the x, y, and z directions can be used to deposit fluid reagents onto the microfluidic chip(s) or substrate(s). The same system may be used to remove fluid (e.g., droplets) from the microfluidic chip(s) or substrate(s). Various non-contact or contact-based fluid dispensing and retrieval systems can be used during the radiolabeling process. These robotic fluid handling devices and methods are well known to those skilled in the art. While an automated, robotic fluid handling system for the depositing and removal of fluid reagents or reaction products is preferred it should be appreciated that the high throughput radiochemistry system may also be used with manual operations. For example, droplets may be added or removed manually using well known pipetting techniques.

While the high throughput chemical synthesis system has been described above in terms of the synthesis of numerous candidate molecules in parallel, e.g. radiolabeling a library of peptides, for a screening experiment such as comparison of in vitro or in vivo properties, the system has other applications and uses. This includes, for example, the synthesis of numerous known PET tracers in parallel (e.g., the production of multiple tracers with a single piece of instrumentation). Another use or application includes accelerating reaction optimization by enabling synthesis under a wide range of conditions (with replicates) simultaneously. Further, as noted herein, the chemical synthesis system may be used for non-radiochemical-based synthesis reactions. For example, the chemical synthesis system may be used for organic chemistry synthesis where multiple steps are used. The chemical synthesis system can be used to screen or optimize reaction conditions with only minor consumption of reagents to ensure that more optical reaction conditions are chosen before risking larger batches of reagents or reactants.

One use of multiple-tracer synthesis capability is to increase the capacity of a radiopharmacy in terms of number of different PET tracers that can be produced in a single day (or a single discrete time period). Typically, a radiopharmacy currently uses one (1) hot cell and one (1) synthesizer per tracer, a very expensive approach to synthesizing multiple different tracers. If instead many (e.g., several, tens, dozens, or hundreds) of different tracers could be made simultaneously on a single platform, potentially the platform could be used for production of preclinical or clinical doses or larger batches of many tracers in a single hot cell. Another use of parallel synthesis capability is to optimize the reaction conditions, as occurs when developing novel PET tracers or when translating macroscale synthesis protocols into the microdroplet format. However, synthesis optimization is hindered by practical limitations on the number of synthesis that can be performed per day using current radiosynthesis apparatus. Thus, a platform that can enable rapid screening of multiple conditions in parallel (e.g., reaction time, reaction temperature, reagent concentration, reagent/precursor volume, reagent solvent type, quantity of radioisotope, salt type and/or phase transfer catalyst, concentration of salts and/or phase transfer catalyst, precursor concentration, type of concentration/dilution solution, etc.) and greatly accelerates optimization. The platform may also be used to optimize additional reaction steps such as type of deprotectant, concentration of deprotectant, deprotection reaction time, deprotection reaction temperature, and the like).

The high throughput radiochemistry system may have a number of sub-systems that operate cooperatively together. The reaction array, as explained above, includes one or more microfluidic chip(s) or substrate(s) each having, in one embodiment, a plurality or reaction sites formed thereon. Alternatively, there could be a plurality of microfluidic chips each having a single reaction site operatively in parallel. The one or more microfluidic chip(s) or substrate(s) are disposed atop a heater platform that contains one or more heaters therein. Another sub-system includes a reagent loading system. This may include a dispensing "head" with multiple non-contact solenoid-valve dispensers as well as a micropipette head. The non-contact dispensers are faster, but limited in number. The pipette tips allow situations (e.g., screening numerous labeled compounds) where there may be dozens or hundreds of different precursors in a microwell plate that should each be loaded to different reaction sites in the reaction array. The pipette system can also collect the final reaction product (or diluted final product). In some embodiments, the system may include a robotic system that moves in the x, y, and z directions to move the reagent delivery head among the reagent sources (e.g., well plates) and reaction sites (located on the microfluidic chip(s) or substrate(s)) and a pipette tip rack. Yet another sub-system may include an output system for final analysis and/or processing of the final product. Each collected reaction product can be sampled and spotted on an array of thin layer chromatography (TLC) plates for radio-TLC analysis, or the system can be coupled with a high-speed chromatography system for analysis or purification (e.g., high performance liquid chromatography (HPLC) or ultra-performance liquid chromatography (UPLC)). In the case of purification, the collected fraction will also require formulation (e.g., evaporation of UPLC mobile phase and resuspension in saline) and an additional round of UPLC analysis (to confirm purity).

Advantages of the system include the ability to perform microscopic radiochemical reactions which significantly reduces the cost of reagents. Using microliter scale reactions, <1% of the amount of reagents used for macroscale reactions are needed while maintaining similar or higher concentrations. When radiolabeling a set of new compounds for screening/evaluation, this advantage reduces the amount of precursor that must be produced for each candidate compound. Alternatively, for reaction optimization experiments, all reactions can be performed from a single batch of precursor and radioisotope. (Using macroscale radiochemistry apparatus, a single data point would require a full batch of precursor and radioisotope.). The system is also time efficient. With the design that includes a sixteen (16) reaction site chip, 4-heater platform), up to sixty-four (64) reactions can be performed simultaneously (four microfluidic chips*16 reaction sites/microchip). This enables several reaction conditions to be optimized in a single day (including replicates). Performing a similar scale optimization with conventional macroscale apparatus could take weeks or months. In addition, reactions can be performed on the same day, with the same batch of reagents and radioisotope, minimizing variables and actually reducing the number of experiments that need to be performed to understand the influence of each reaction variable. This is because there can be day-to-variations in the quality of the radioisotope solution (e.g. different lots or containers of reagent may have different impurity profiles, or the reagent may degrade over time).

In one embodiment, a high throughput chemical synthesis system includes a heater platform containing one or more heaters therein and defining an upper surface configured to hold at least one microfluidic chip or substrate thereon, wherein the at least one microfluidic chip or substrate comprises a plurality of reaction sites formed thereon. The system includes a cooling device in thermal contact with the heater platform.

In another embodiment, a high throughput radiochemistry system includes a heater platform containing one or more heaters therein and defining an upper surface configured to hold a plurality of microfluidic chips or substrates thereon, wherein the plurality of microfluidic chips or substrates have a plurality of reaction sites formed thereon, the heater platform containing a plurality of independently controllable heaters. One or more cooling devices are in thermal contact with the heater platform. A robotic system is provided for reagent dispensing and product collecting/sampling, the robotic system comprising a robotic moveable gantry configured to move in the x, y, and z direction and having a pipette/dispenser head secured to the moveable gantry, the pipette/dispenser head having a plurality of dispensers and a pipette cone disposed therein. The robotic system includes one or more microplate storage areas and at least one or more pipette tip racks.

In another embodiment, a method of performing radiochemical synthesis using the systems disclosed herein includes loading one or more reagents or radiochemical precursors on the plurality of reaction sites with the pipette/dispenser head and subjecting the one or more reagents or radiochemical precursors to one or more temperature-controlled operations while disposed on the heater platform to synthesize a radiochemical product.

In another embodiment, a method of performing radiochemical synthesis using the systems disclosed herein includes loading one or more microfluidic chips or substrates on the heater platform; loading one or more reagents or radiochemical precursors on the plurality of reaction sites with the pipette/dispenser head; and subjecting the one or more reagents or radiochemical precursors to one or more temperature-controlled operations while disposed on the heater platform to synthesize a radiochemical product.

BRIEF DESCRIPTION OF THE DRAWINGS

FIG. 1A illustrates a top down view of a microfluidic chip or substrate according to one embodiment. In this embodiment, there are four (4) reaction sites.

FIG. 1B illustrates a side view of the microfluidic chip or substrate of FIG. 1A.

FIG. 1C illustrates a top down view of a microfluidic chip or substrate according to another embodiment.

FIG. 2A also illustrates optional exhaust vents formed in the heater platform to aid in exhausting heated air.

FIG. 11A (top) is a schematic of an experiment with a pattern of loaded (with radioisotope) and blank (loaded with solvent only) reaction sites. (bottom) Cerenkov image of the chip after drying the droplets. FIG. 11B (top) is a schematic of an experiment with a different pattern of loaded and blank reaction sites. (bottom) Cerenkov image of the chip after drying. FIG. 11C (top) is a schematic of experiment to test repeatability during synthesis of [$^{18}$F]Fallypride (240 nmol TBAHCO$_3$ amount for top two rows and 7 nmol TBAHCO$_3$ amount for bottom two rows). (Bottom) Cerenkov image of the chip after the collection step.

DETAILED DESCRIPTION OF ILLUSTRATED EMBODIMENTS

Figure 2A:
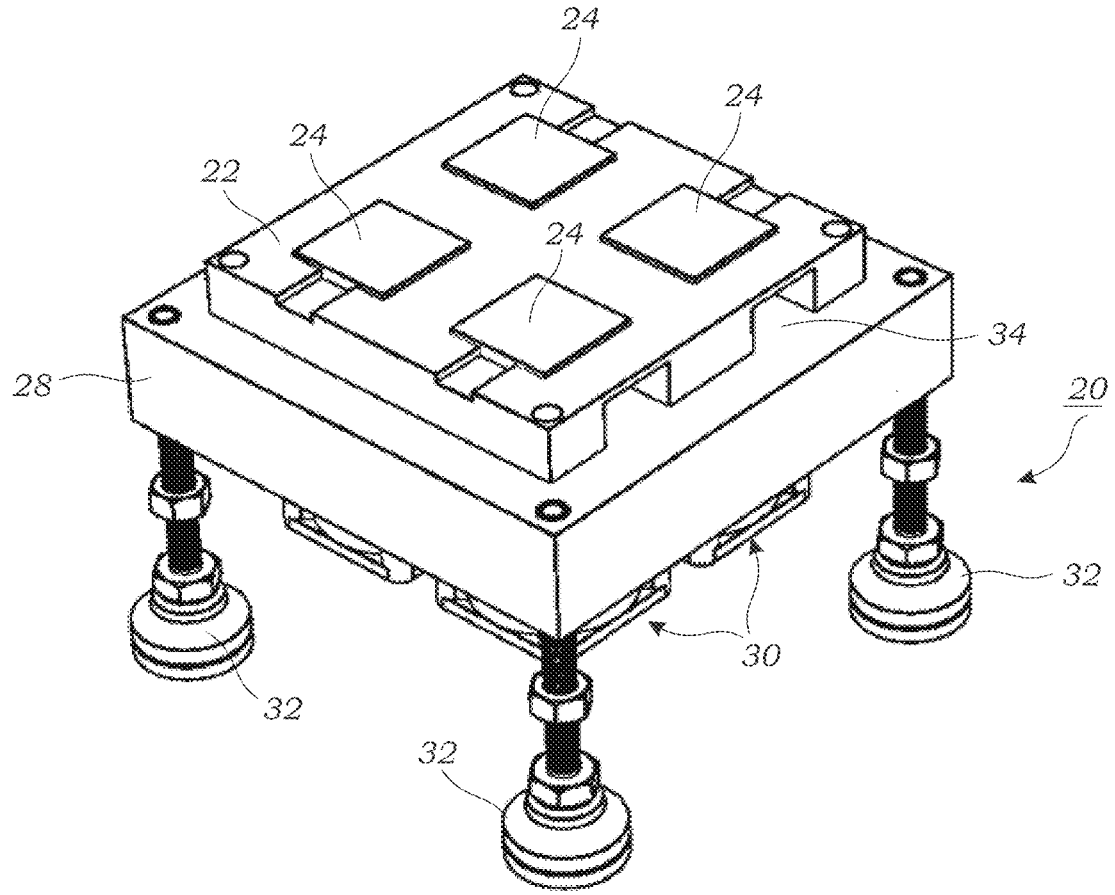
FIG. 2A illustrates one embodiment of a multi-heater system that uses four (4) heaters.

FIGS. 1A-1C illustrates microfluidic chip or substrate 10 that is used to perform small volume chemical reactions. In one particular embodiment, the microfluidic chip or substrate 10 is used for radiochemistry synthesis or other reactions. The microfluidic chip or substrate 10 may be made hydrophilic material (e.g., silicon, glass) and coated with a hydrophobic coating 12 such as PTFE (e.g., Teflon®) or other fluoropolymer. For example, standard photolithographic methods such as those disclosed in Wang et al. may be used to coat the microfluidic chip or substrate 10. See e.g., Wang et al., Performing multi-step chemical reactions in microliter-sized droplets by leveraging a simple passive transport mechanism, Lab Chip, 2017, 17, 4342-4355, which is incorporated herein by reference. An exemplary thickness of the hydrophobic coating 12 may be from around 50 nm to around several hundred nm, although the invention is not so limited. The hydrophobic coating 12 is etched or otherwise removed at different locations to create individual reaction sites 14 that hold the small volumes of liquid as described herein. The individual reaction sites 14 are hydrophilic regions on the microfluidic chip or substrate 10. The microfluidic chip or substrate 10 includes a plurality of reaction sites 14 formed thereon.

Each reaction site 14 is a shallow cylindrical "well" that holds the liquid volume. In one particular embodiment that uses four (4) reaction sites on a single microfluidic chip or substrate 10, the thickness of the hydrophobic coating 12 was about 127±6 nm (n=4), which determined using a stylus profiler (Dektak 150 Surface Profiler, Plainview, NY, USA. The microfluidic chip or substrate 10 used for experiments described herein was 25 mm×27.5 mm with four (4) hydrophilic reaction sites 14 (diameter of 4 mm). Of course, it should be appreciated that other geometries and dimensions may be used for the microfluidic chip or substrate 10 and the reaction sites 14 including additional hydrophilic reaction sites 14 as explained herein. For example, FIG. 1C illustrates an embodiment that includes sixteen (16) different reaction sites 14. It should be appreciated that any number of multiple reaction sites 14 may be formed on the microfluidic chip or substrate 10. For example, there may be 4, 6, 8, 10, 12, 14, 16, 18, 20 or more reaction sites 14 on a single microfluidic chip or substrate 10. Of course, odd numbers of reaction sites 14 may also be used.

Although each reaction site 14 is a shallow cylindrical "well" (with volume ~1.6 µL for a 4 mm diameter spot on a 2×2 microfluidic chip or substrate 10, and ~0.90 µL for a 3 mm diameter spot on a 4×4 microfluidic chip or substrate 10), each reaction site 14 can actually hold significantly more volume by acting as a "hydrophilic trap." Depending on the properties of the liquid, droplets up to ~40 µL could be loaded into the 4 mm diameter reaction sites 14 without overflowing onto the surrounding hydrophobic region.

To prepare the 25 mm×27.5 mm tested microfluidic chips or substrates 10, a silicon wafer was spin-coated with Teflon® AF 2400 (Dupont) to form a hydrophobic coating 12 of 150 nm thickness, followed by photoresist (SPR220-7, MicroChem). The photoresist was exposed to UV with the designed mask and developed in MF-26A developer. This layer then acts as an etch mask for subsequent dry-etching for patterning the Teflon®. Finally, the wafer was diced, and photoresist stripped from the microfluidic chips or substrates 10 with acetone and isopropanol.

With reference to FIGS. 2A-2D, one embodiment of a high throughput radiochemistry system 20 is disclosed for performing reactions on one or more microfluidic chip or substrates 10. The system 10 includes a heater platform 22 that includes one or more heaters 24 disposed therein. The one or more heaters 24 are preferably individually controllable such that the temperature(s) of the one or more can be separately controlled. As explained herein, one or more microfluidic chips or substrates 10 are placed atop the one or more heaters 24. Thus, the one or more microfluidic chips or substrates 10 may rest atop the one or more heaters 24 and are in thermal contact with the same. This includes direct contact between the one or more microfluidic chips or substrates 20 and the one or more heaters 24 as well as indirect contact (e.g., an intervening layer or material or even gas layer interposed between the one or more microfluidic chips or substrates 10 and the one or more heaters 24). Portions of the one or more microfluidic chips or substrates 10 may also contact the heater platform 22. In one embodiment, each microfluidic chip or substrate 10 is associated with a single heater 24. For example, in one particular embodiment, there are four (4) microfluidic chips or substrates 10 and four (4) heaters 24 with each microfluidic chip or substrate 10 being associated with its own heater. Of course, in other embodiments, multiple microfluidic chips or substrates 10 may be located over or associated with a single heater 24.

The one or more heaters 24 are embedded or potted within the heater platform 22 according to one embodiment. The material of the heater platform 22 is preferably a thermally insulating material such as a ceramic or calcium silicate. An example of a material that can be used for the heater platform 22 is Firetemp® X which is an inorganic, noncombustible high temperature insulation material made primarily of lime, silica, and reinforcing fibers. The insulating material of the heater platform 22 prevents heat from one heater from transferring to another separate microfluidic chip or substrate 10 (e.g., prevents thermal crosstalk).

FIGS. 2A-2E illustrate an embodiment of a system 10 that includes four (4) heaters 24 disposed in the heater platform 22. The heaters 24 are each electrically powered via wires 26 (seen in FIG. 2E) that are coupled to an electrical power source and driver circuitry (see FIG. 7). The heater platform 22 in this embodiment is secured to an optional base 28 onto which one or more cooling devices 30 are mounted. In this embodiment, the cooling devices 30 are in the form of fans. The fans 30 in this embodiment, blow ambient air against the one or more heaters 24 to cool the same during cooling operations. In the embodiment, of FIGS. 2A-2D, each heater 24 is associated with its own fan 30 to provide cooling. As explained herein, the fan is electrically powered and controlled to provide the ability to cool or ramp down the temperature of the reaction sites 14 as needed. Note that the fans 30 may mount directly to the heater platform 22 or through the base 28 that is itself secured to the heater platform 22. The base 28 may be made out of a different material such as a polymer or the like.

Figures 2B, 2C, 2D:
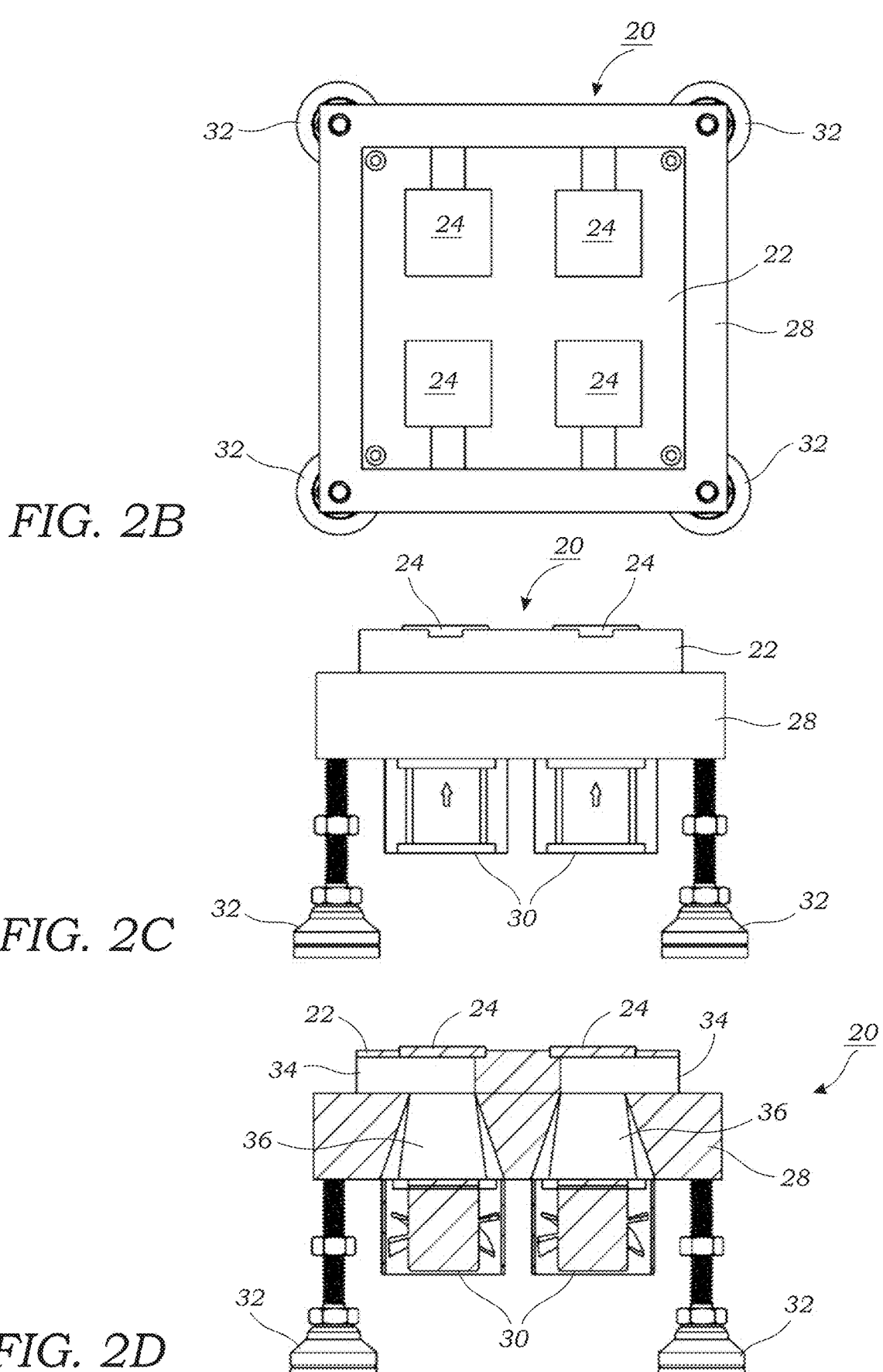
FIG. 2B illustrates a top view of the heater platform.
FIG. 2C illustrates a side view of the multi-heater platform.
FIG. 2D illustrates a sectional view of the heater platform of FIGS. 2A-2C showing the flow path of air through the fan base and out the exhaust vents.
Figure 2E:
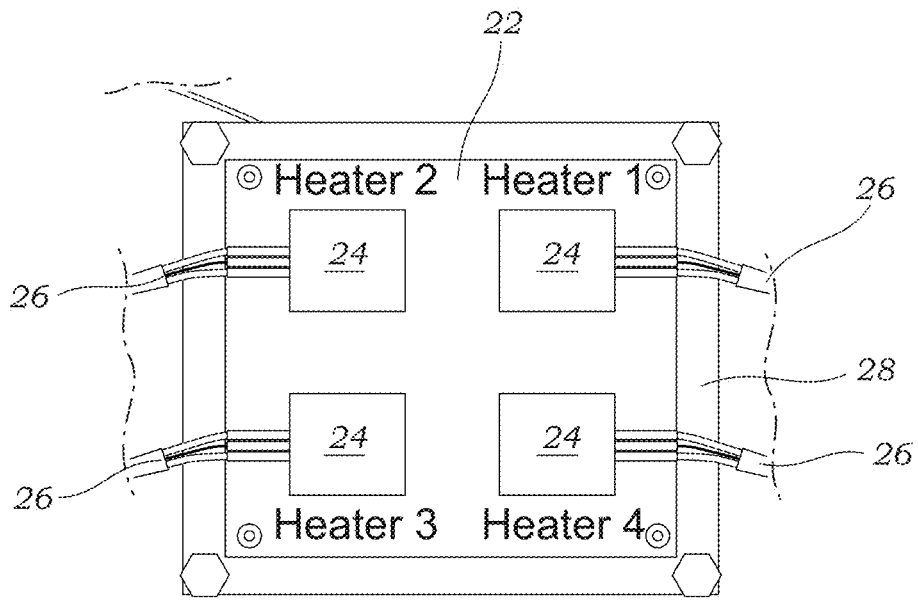
FIG. 2E is an illustration showing four (4) heaters in the heater platform.

As seen in FIGS. 2A-2D, the heater platform 22 is supported by a plurality of stands 32 (four in this embodiment) located at the four corners of the heater platform 22. The stands 32 elevate the heater platform 22 and provide room for the fans 30. The fans 30 are situated below each heater 24 on the base 28 to facilitate cooling when needed. With reference to FIGS. 2A and 2D, the heater platform 22 includes optional exhaust vents 34 to aid in reducing cooling time. The exhaust vents 34 aid in evacuating heat from adjacent the heater 24 to the external environment. In the embodiment of FIGS. 2A-2D, there are four (4) exhaust vents 34 with one vent 34 associated with each heater 24. Of course, additional or fewer vents 34 (or no vents 34) may be used. During operation, the fans 30 blow air from the bottom through air flow passages formed in the base 28 and then against the bottom of the heater 24 and out the vents 34. Other features may be incorporated into the heater platform 22 and/or base 28 to direct airflow over a surface of the heater(s) 24.

Figure 3:
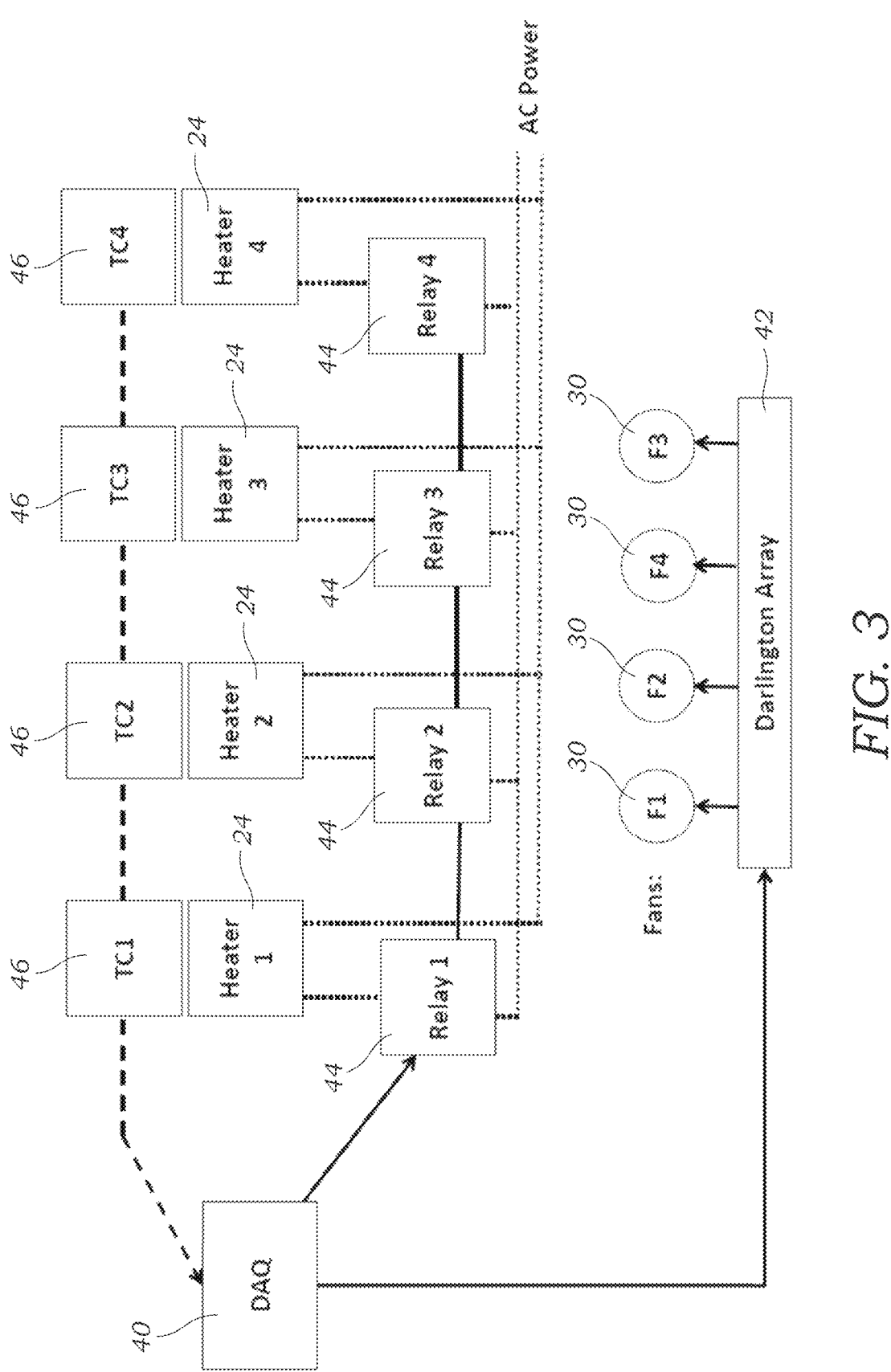
FIG. 3 illustrates the wiring schematic used to control the four heaters and fans using a DAQ module and fan speed control circuitry (Darlington).

The heaters 24 may include high-power ceramic heaters such as Watlow advance ceramic heaters ~23 mm wide and ~23 mm long, although they are not limited to a specific manufacturer or brand. Each of the four (4) heaters 24 was mounted in a heater platform 22 made from ceramic insulating material. FIG. 3 illustrates one embodiment of a wiring schematic used to control the four heaters 24 and fans 30 using a data acquisition (DAQ) module 40 and fan speed control circuitry 42 (e.g., Darlington). Relays 44 are used to drive heaters 24. Currently may be supplied in an ON/OFF fashion via the relays 44 to reach or maintain the desired temperature. Alternatively, voltage/current applied to the heater(s) 24 may be altered using a proportional-integral-derivative (PID) control or any other temperature control scheme. Temperatures are monitored via thermocouples 46 that may be integrated into the heaters 24. Here, the signal from a thermocouple 46 (which was integrated in the heater 24) was amplified through a thermocouple amplifier (such as amplifier 148 in FIG. 7) and read by a data acquisition (DAQ) module 40. A digital output 48 of the DAQ module 40 was used to control the supply of 120 VAC to each heater for feedback control of the temperature. Due to the rapid response of the heaters 24, an on-off temperature controller was found to be sufficient to achieve stable temperatures. Each individual fan 30 could be controlled by activating the power supply via digital output-controlled fan speed control 42 (e.g., Darlington array).

To use the system 20, fluid droplets that contain reagents, precursors, solvents, or wash solutions are loaded onto the reaction sites 14 on the one or more microfluidic chips or substrates 10. Likewise, products that are generated at the reaction sites 14 may be removed from the reaction sites 14. In one embodiment, fluid droplets are loaded and/or removed via a manual operation. This may be done, for example, using a pipette, syringe, or the like. In another embodiment, as described further herein, a robotic fluid handling system FIGS. 4A-4I, 5A-5B, 6, 7 may be provided to load/remove fluid form the microfluidic chip(s) or substrate(s). Regardless of whether the loading or removal of fluid to/from the reaction sites 14, the one or more heaters 24 in the system 20 are used to perform one or more temperature-controlled operations. This includes operations such as heating, cooling, temperature maintenance, evaporation, and boiling. The system 20 may be programmed to adjust temperatures quickly as needed. This includes quickly ramping up/down temperatures to accommodate the particular reaction conditions needed to be performed. Temperatures may also be maintained at a certain temperature or setpoint for a period of time.

In one embodiment, all the reaction sites 14 associated with a particular heater 24 and loaded with reagents proceed in parallel with one another. Alternatively, a sequential operation may be used where a fraction of the reaction sites 14 in a microfluidic chip or substrate 10 are heated followed by loading of a remaining fraction of the reaction sites 14 and then subject to another heating operation. This later approach enables one to obtain more reaction times and temperatures out of a single heater 14 with the tradeoff of losing some parallelism.

The heaters 24 may be calibrated to ensure that the desired temperatures can be maintained as needed. For example, each heater 24 can be immersed into a well-stirred oil-bath and the temperature monitored using the built-in thermocouple 46 using a calibrated meter. For several different settings of the hotplate or oven, the oil temperature is recorded using a calibrated thermometer along with the steady-state temperature of the heater thermocouple 46. From two or more points, a calibration curve (e.g., linear) can be generated relating the signal from the integrated thermocouple 46 to the average heater temperature.

The heaters 24 may also be calibrated by coating the same with a material of well-defined emissivity (e.g., commercially available optical black paints). The average surface temperature of the heater 24 can be monitored with an infrared camera. Each heater 24 is heated to different temperatures using heater control circuitry, and both the surface temperature (via thermal camera) and internal temperature (via integrated thermocouple 46) are recorded. From two or more points, a calibration curve (e.g., linear) can be generated relating the signal from the integrated thermocouple 46 to the heater average surface temperature. Of course, other calibration techniques known to those skilled in the art may be used.

The systems 20, 60 described herein may be used in a number of applications including but not limited to reaction optimization and for the synthesis of multiple different compounds for screening studies. As explained herein, one particular application involves the synthesis of radiochemicals and/or radiopharmaceuticals but the systems have application to any small volume fluid synthesis. An example would be to perform screening of reaction conditions for a particular step in a long multi-step organic synthesis sequence. The small-scale reactions do not consume very much reagent but would provide useful information on how to optimally proceed (with the highest yield) during the subsequent steps in the synthesis process. For radiopharmaceuticals, the systems 20, 60 enables the rapid screening of multiple conditions in parallel for the labelling of a library of related compounds for screening/comparison for in vivo and/or in vitro properties. The systems 20, 60 allow for significant space savings as multiple compounds may be labelled within a single hot/mini-cell 150 to increase the variety and/or capacity of PET tracers produced at a radiopharmacy. Different conditions or parameters include, for example, reaction time, reaction temperature, reagent concentration, reagent/precursor volume, reagent solvent type, quantity of radioisotope, salt type and/or phase transfer catalyst, concentration of salts and/or phase transfer catalyst, precursor concentration, type of concentration/dilution solution, etc. and greatly accelerates optimization. The platform may also be used to optimize additional reaction steps such as type of deprotectant, concentration of deprotectant, deprotection reaction time, deprotection reaction temperature, and the like). Examples of radiochemicals that may be synthesized with the systems 20, 60 include, for example, [18F]Fallypride and [18F]Flumazenil, [18F]FDOPA, [18F] FET, [18F]Florbetaben, [18F]PBR06. Other compounds labeled with fluorine-18, or compounds labeled with other radioisotopes, can also be synthesized with the system.

While the cooler device(s) 30 may include one or more fans in certain embodiments, in other embodiments, the cooler(s) 30 may include one or more of a heat sink, heat pipe, liquid cooler, evaporative cooling, and thermoelectric cooler. In some embodiments, fans may be incorporated with these other cooling device 30 modalities.

FIGS. 4A-4I, 5A-5B, 6, 7 illustrates various aspects of another embodiment of a robotic system 60 that incorporates the heater platform 22 and one or more heaters 24 as previously described herein. In the robotic system 60 embodiment, the robotic system 60 incorporates various robotic controls and functions for reagent dispensing and product collecting/sampling. With reference to FIG. 4, the robotic system 60 has a frame 62 that holds the various components. The frame 62 includes a top 62t, base plate or bottom 62b, sides 62s, back braces 62b. The front may be open to provide access to the inside to load the device with well plates 66, pipette tips 68, TLC plates 72, microfluidic chips or substrates 10 and the like, although in other embodiments, the front may be fully or partially enclosed. The robotic system 60 is preferably small enough to fit within the space of a conventional "hot cell" or "mini-cell". Exemplary dimensions of the frame 62 include a height of around 56 cm, a width of around 64 cm, and a depth of around 41 cm. Of course, other dimensions are contemplated. In another embodiment, the frame components could be integrated directly into the hot cell or mini-cell.

The base plate or bottom 62b of the frame 62 is provided with nests 64 that act as respective holding areas for microwell plates 66 (two are illustrated in FIG. 4), a pipette tip rack 68, and optionally a TLC plate holder 70 that holds one or more TLC plates 72. In some embodiments, the TLC plate holder 70 may be omitted and/or replaced with another microwell plate 66. The base plate or bottom 62b of the frame also supports the heater platform 22 and one or more heaters 24 as previously described. As seen in FIG. 4A, the heater platform 22 contains four (4) different heaters 24 with one heater 24 illustrated being loaded with a microfluidic chip or substrate 10. The heater platform 22 and heaters 24 are formed as described herein and include one or more cooling devices 22.

Figure 4A:
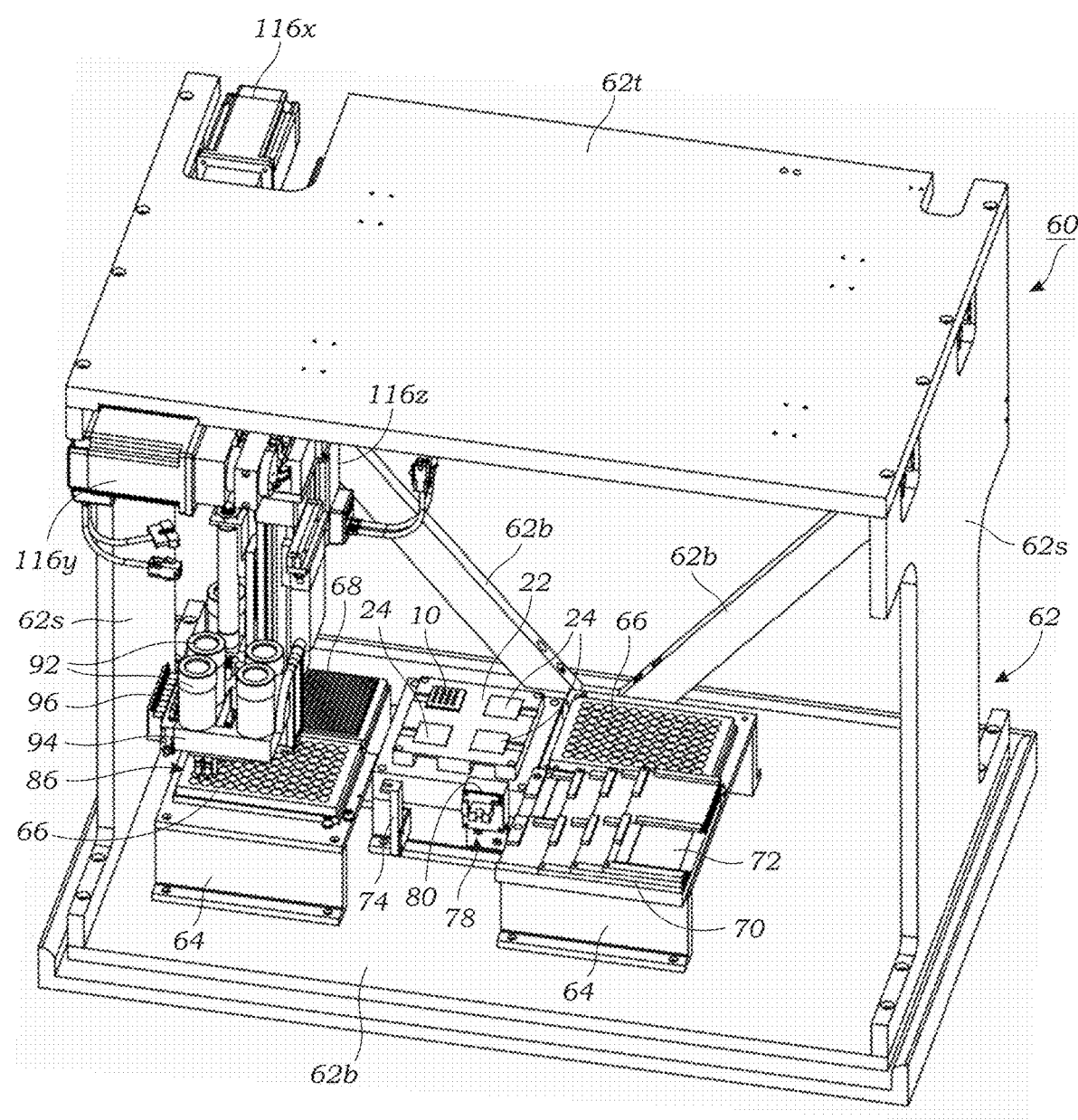
FIG. 4A illustrates a perspective view of an automated robotic system for high throughput chemical synthesis.
Figures 4B, 4C, 4D:
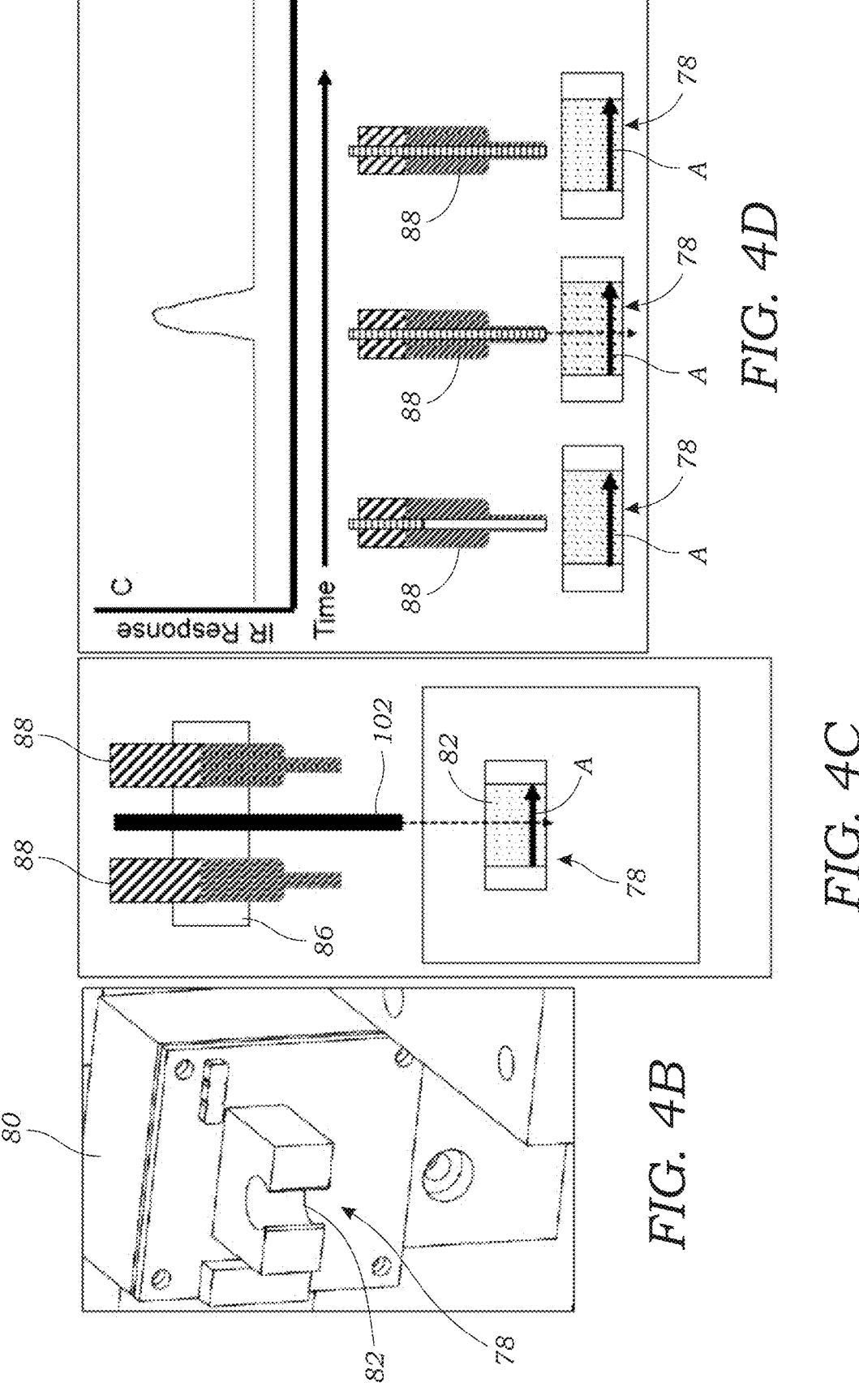
FIG. 4B illustrates a perspective view of the priming sensor used in the automated robotic system of FIG. 4A.
FIG. 4C schematically illustrates the priming sensor used to detect fluid flow (dashed arrow) emitted from the pipette cone.
FIG. 4D schematically illustrated the priming sensor used to detect fluid flow (dashed arrow) emitted from the dispenser. Also illustrated is an illustrative signal output from the priming sensor showing the change in signal that is associated with the flow of fluid through the notch or opening in the priming sensor.

The base plate or bottom 62b of the frame 62 also supports a fork 74 (also illustrated in FIGS. 4A, 4B, 4E), which as described herein is used to remove the pipette tip 76 from the pipette cone 102 which is described below. This allows the automated removal of pipette tips 76 as pipette tips 76 are changed between the various dispensing/removal operations performed by the pipette. A waste receptable (not shown) may be located below the fork 74 to capture waste pipette tips 76. The base plate or bottom 62b of the frame 62 also supports (either directly or indirectly—for example, if mounted on the heater base 28) a priming sensor 78. The priming sensor 78 as best seen in FIGS. 4B-4E, includes a base or mount 80 that is secured to the heater base 28. The priming sensor 78 includes a notch or partial opening 82 that is used to sense the passage of fluid. The priming sensor 78 operates by emitting a beam of light (e.g., infrared light indicated by arrow A from a light emitting diode) across the notch or partial opening 82 that is captured by a detector (e.g., photodiode) located on the opposite side of the notch or partial opening 82. Liquid flow is detected by the priming sensor 78 when the light signal as measured by the detector aspect of the priming sensor 78 senses a rapid change in signal. FIG. 4D illustrates a graph of detected light signal as a function of time and shows a pulse indicating the passage of fluid through the notch or partial opening 82. A waste receptacle (not shown) may be placed below the notch or partial opening 82 to catch waste fluid. Of course, the priming sensor 78 may also operate using other detection schemes such as mass detection (e.g., under waste receptacle) or capacitive detection.

Figure 4E:
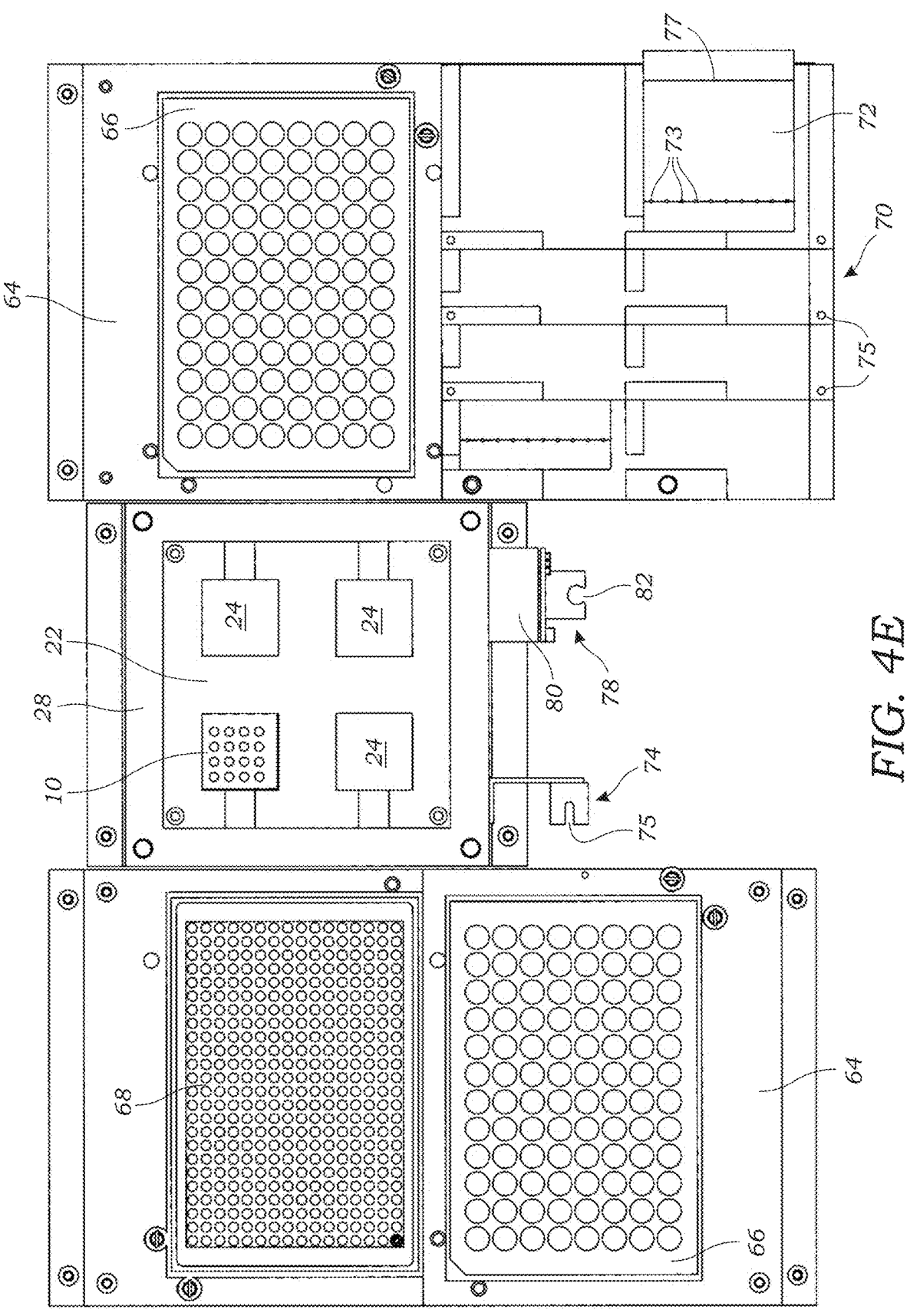
FIG. 4E illustrates a top down plan view of the layout of the various working areas of the automated robotic system for high throughput chemical synthesis. Two microwell plates are illustrated along with a pipette tip rack that holds pipette tips. A heater platform with four (4) heaters is illustrated with one being occupied by a microfluidic chip. A TLC holder loaded with TLC plates is also illustrated. The fork used to remove pipette tips is also visible along with the priming sensor.

FIG. 4E illustrates a top down view of the base plate or bottom 62b of the frame 62 showing the nests 64 that hold the microwell plates 66 (two are illustrated in FIG. 4B), the pipette tip rack 68 that holds pipette tips 76, the TLC plate holder 70 that holds one or more TLC plates 72. Also illustrated is the heater platform 22 with four (4) heaters 24 with a microfluidic chip or substrate 10 located on one of the heaters 24. The pipette removal fork 74 and the priming sensor 78 are also illustrated. This region of the robotic system 60 effectively operates as a working area where fluids are dispensed/removed.

Figure 4F:
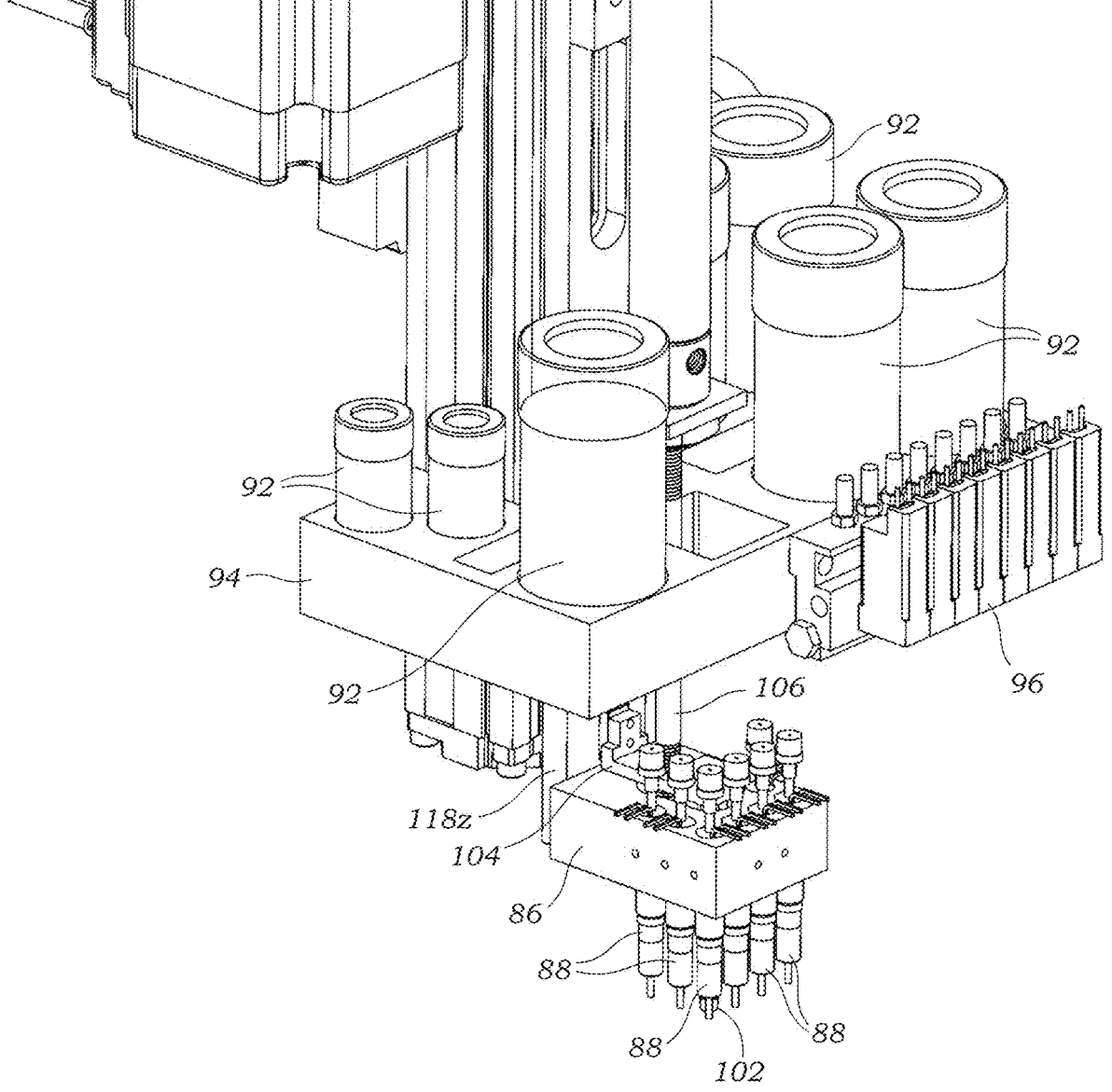
FIG. 4F illustrates a perspective view of the pipette/dispenser head that is mounted on the moveable gantry (x, y, z directions) according to one embodiment.
Figure 4G:
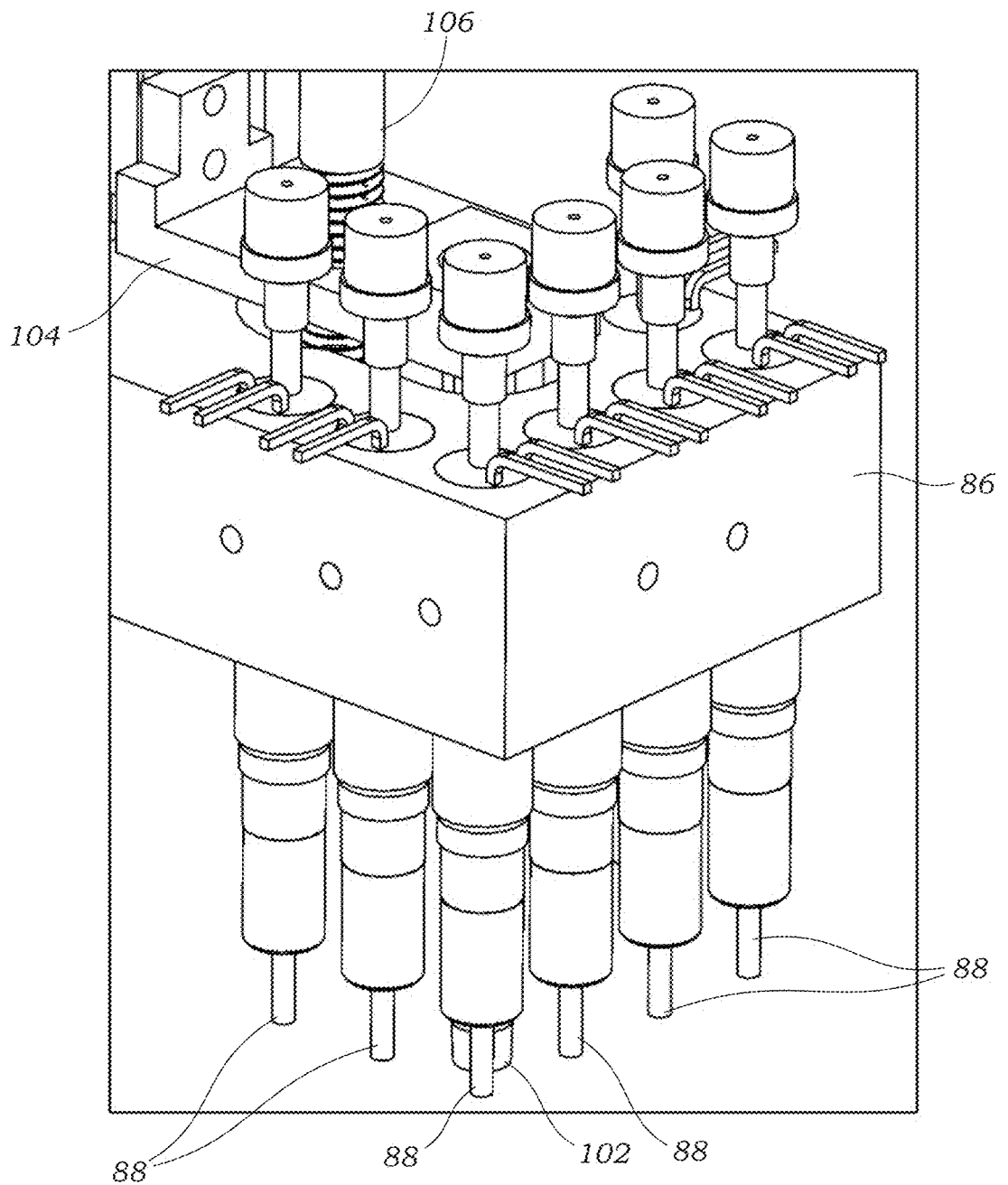
FIG. 4G is a close-up view of the pipette/dispenser head. Also illustrated is the pipette cone and actuator used to move the same via the bracket structure.
Figure 4H:
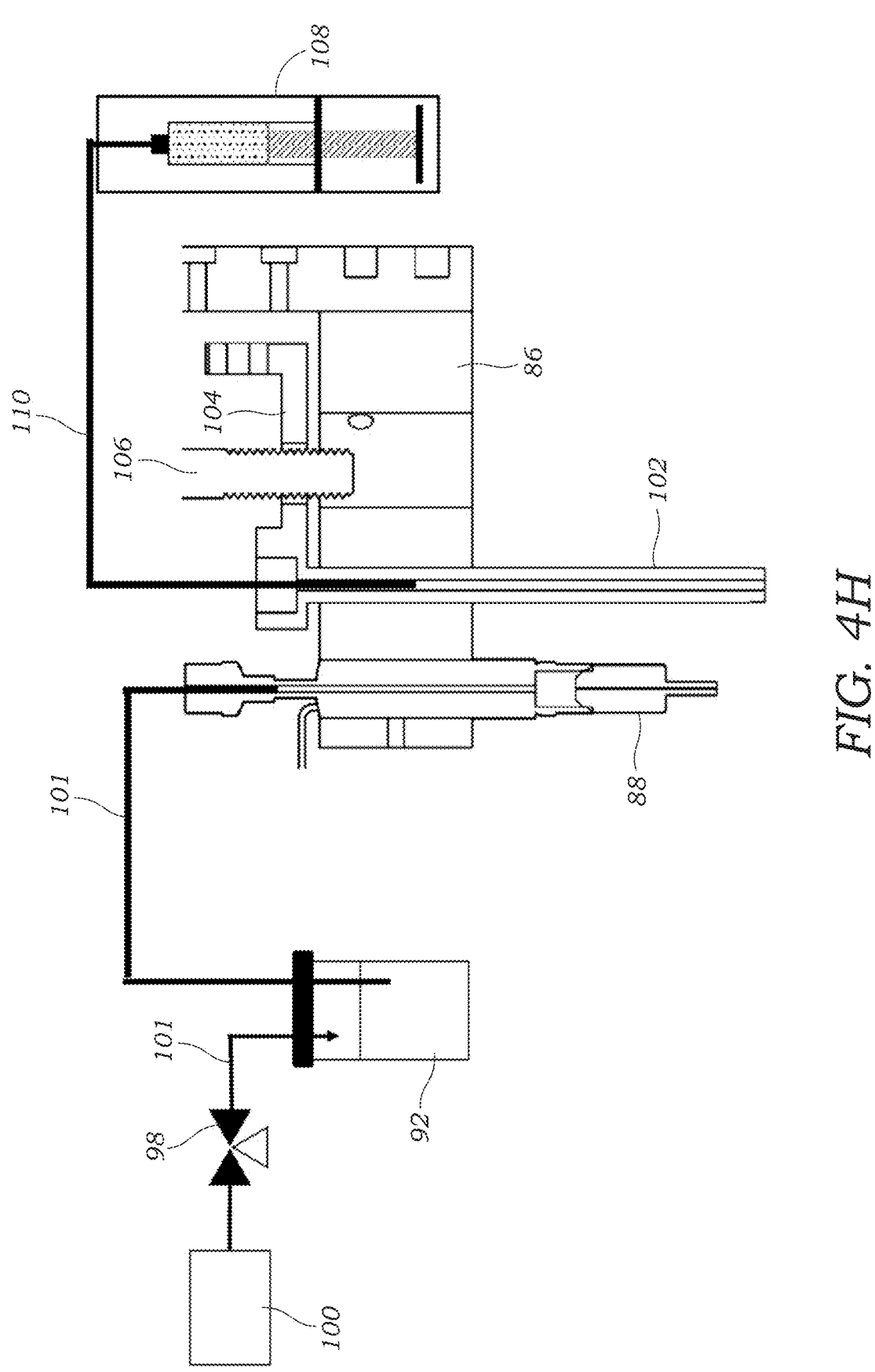
FIG. 4H schematically illustrates a single dispenser connected to a reagent vial and pressured gas source that is used to push fluid into the dispenser. Also illustrated is a pump (e.g., syringe pump) that is used to eject fluid/withdraw fluid using the pipette cone/pipette tip (pipette tip removed in this view).

Referring back to FIG. 4A, the robotic system 60 includes a robotic moveable gantry 84 that is configured to move in the x, y, and z directions and includes a pipette/dispenser head 86 that is coupled to the moveable gantry 84 that also moves in the x, y, and z directions in response to movement of the gantry 84. The pipette/dispenser head 86 is best seen in FIGS. 4F and 4G and includes a plurality of dispensers 88 secured to the pipette/dispenser head 86. The dispensers 88 may include non-contact solenoid-valve type dispensers and are electrically actuated via electrical connections 90. The fluid for each non-contact dispenser 88 is contained in reagent vials 92 (e.g., 2 mL or 20 mL vials) that are contained in a vial holder 94 that is secured to the moveable gantry 84. A valve manifold 96 is secured to the vial holder 94 and includes a plurality of valves 98 (FIG. 4H) therein that permit the valved flow of gas from a gas source 100 (e.g., tank or pressurized wall source) into the head space of the reagent vials 92 via tubing or conduit 101. This pressurized head space then pushes liquid reagent from the respective reagent vial 92 to the associated non-contact dispenser 88. Flexible tubing or conduit 101 is used to transmit the fluid from the reagent vials 92 to the dispensers 88 as seen in FIG. 4H. While non-contact, solenoid-valve type dispensers 88 are illustrated these may be replaced by other dispenser types such as microfluidic dispensers, ink-jet style dispensers or printing heads.

As best seen in FIGS. 4G and 4H, the pipette/dispenser head 86 includes a pipette cone 102 that is part of the robotic pipette device that is loaded with pipette tips 76 from the pipette tip rack 68 (e.g., 384 pipette tip rack). The pipette cone 102 is coupled to bracket 104 that is itself secured to an actuator 106. In this regard, the pipette cone 102 can be actuated to move up/down in the z direction (separate and apart from the z direction movement imparted by the moveable gantry 84). This up/down movement of the pipette cone 102 enables the pipette cone 102 to be extended (or actuated in the down state) during use and retracted (or actuated in the up state) when not in use. In particular, in the up state, the tip of pipette cone 102 can be retraced several centimeters so that the pipette cone 102 is out of the way of the dispensers 88. In one embodiment, the actuator 106 is a pneumatic cylinder that allows extension and retraction of the pipette cone 102. This feature allows the pipette tip 76 to be moved up out of the way of the dispensers 88 so that dispensers 88 can closely approach a dispensing location, e.g. a reaction site 14 on a microfluidic chip or substrate 10.

This advantageously allows much greater efficiency of operations such as collecting the crude reaction product from the microfluidic chip or substrate 10, which involves typically 3-4 repeats of (i) dispensing collection solution with a non-contact dispenser 88, (ii) aspirating diluted reaction product with the pipette tip 76, (iii) move to a well plate 66 location, (iv) dispensing the contents of the pipette tip 76. As seen in 4H, the pipette cone 102 includes lumen for the passage of fluid. The pipette cone 102 is coupled to a pump 108 via tubing or other conduit 110. The pump 108 may include a syringe pump but other commercially available pipetting pumping sources or other built-in pump may also be used.

Figure 4I:
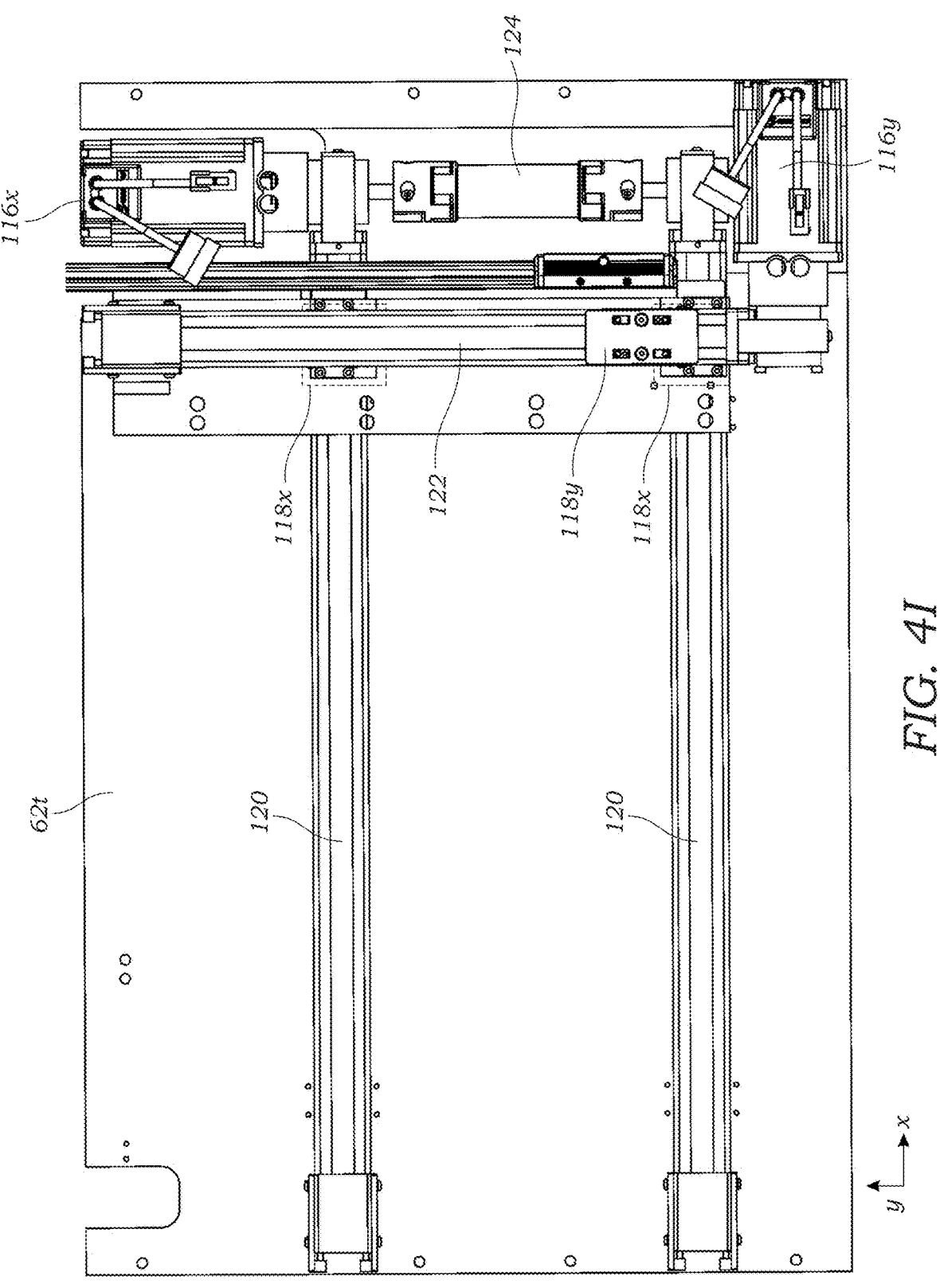
FIG. 4I illustrates the view of the rail-based system used to drive the moveable gantry.

The moveable gantry 84 operates using a series of motors 116x (for x-axis movement), 116y (for y-axis movement), 116z (for z-axis movement). Each motor 116x, 116y, 116z is coupled to a carriage 118x, 118y, 118z via a belt (not shown) (for carriages 118x, 118y) and a leadscrew for carriage 118z. Of course, other drive mechanisms may also be used such as linear motors or the like. The respective carriage 118x, 118y, 118z moves along a rail or slide in the designated direction (i.e., x, y, or z direction). With reference to FIG. 4I, the top 62t of the frame 60 includes a pair of rails 120 that are used to move the x carriages 118x in response to rotation from the motor 116x. A single rail 122 is used for y-directional movement of the carriage 118y in response to rotation from motor 116y as seen in FIG. 4I. A coupler 124 is used to synchronize the belts (not shown) for the carriages 118x, 118y. Motor 116z is used to move the pipette/dispenser head 86 via the carriage 118z.

Figures 5A, 5B:
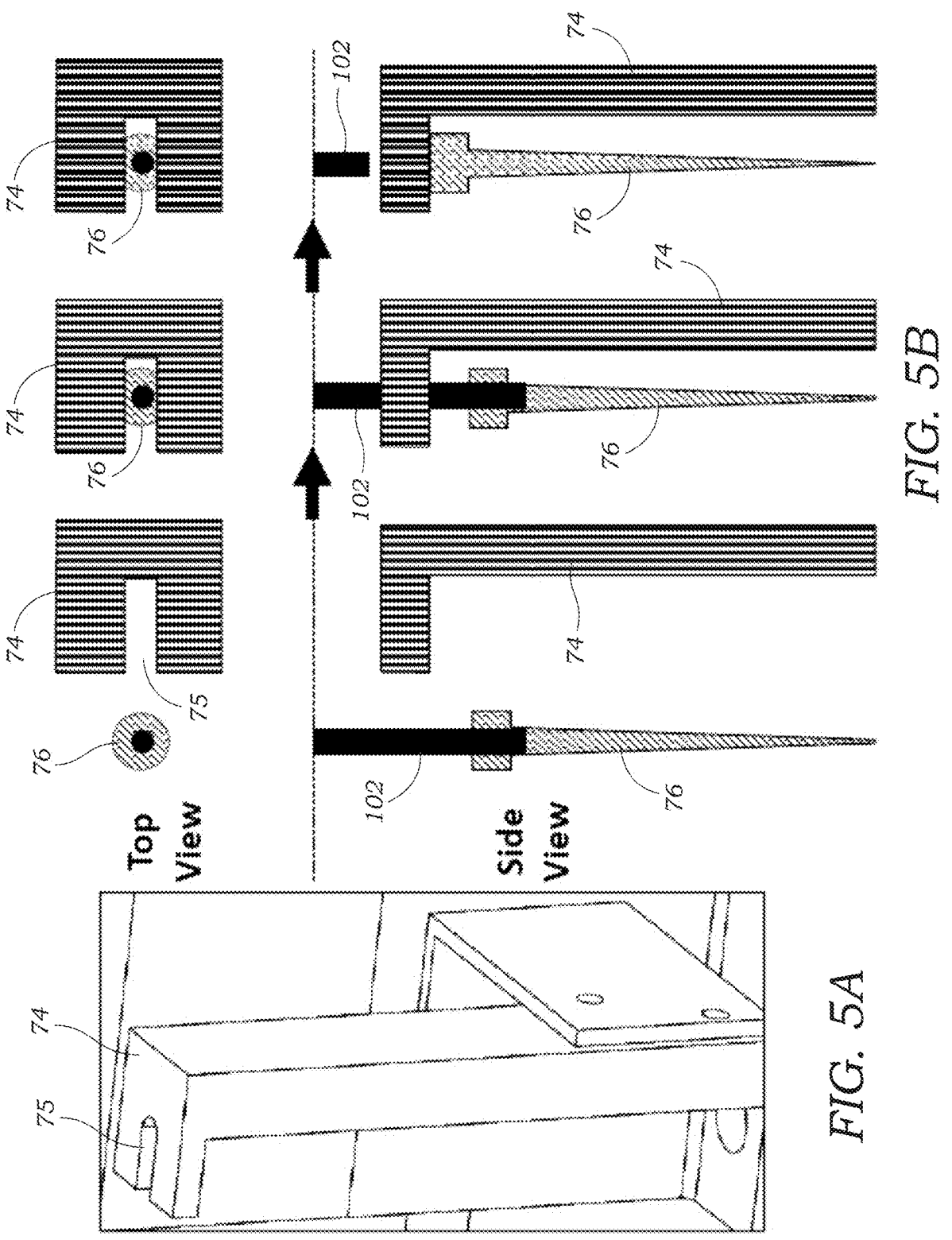
FIG. 5A illustrates a perspective view of the fork used to remove pipette tips from the pipette cone according to one embodiment.
FIG. 5B illustrates the operations used to remove or eject the pipette tip from the pipette tip according to one embodiment.

FIGS. 5A and 5B illustrates pipette removal fork 74 (FIG. 5A) and the sequence of operations used to remove the pipette tip 76. As seen in FIG. 5A, a notch 75 is formed in the fork 14 and is dimensioned to accommodate pipette cone 102 but small enough that the fork 14 prevents the large end of the pipette tip 76 from passing through the notch 75. FIG. 5B shows the sequence of movements of the pipette cone 102 carrying a pipette tip 76 to remove the same. The pipette cone 102 (with the pipette tip 76 mounted thereon) is lowered to place the pipette cone 102 in the notch 75 of the fork 74. The pipette cone 102 is then retracted upward until the pipette tip 76 contacts the tines forming the notch 75 and is stopped from further movement. Additional retraction of the pipette cone 102 will then eject the pipette tip 76 from the end of the pipette cone 102.

Figure 6:
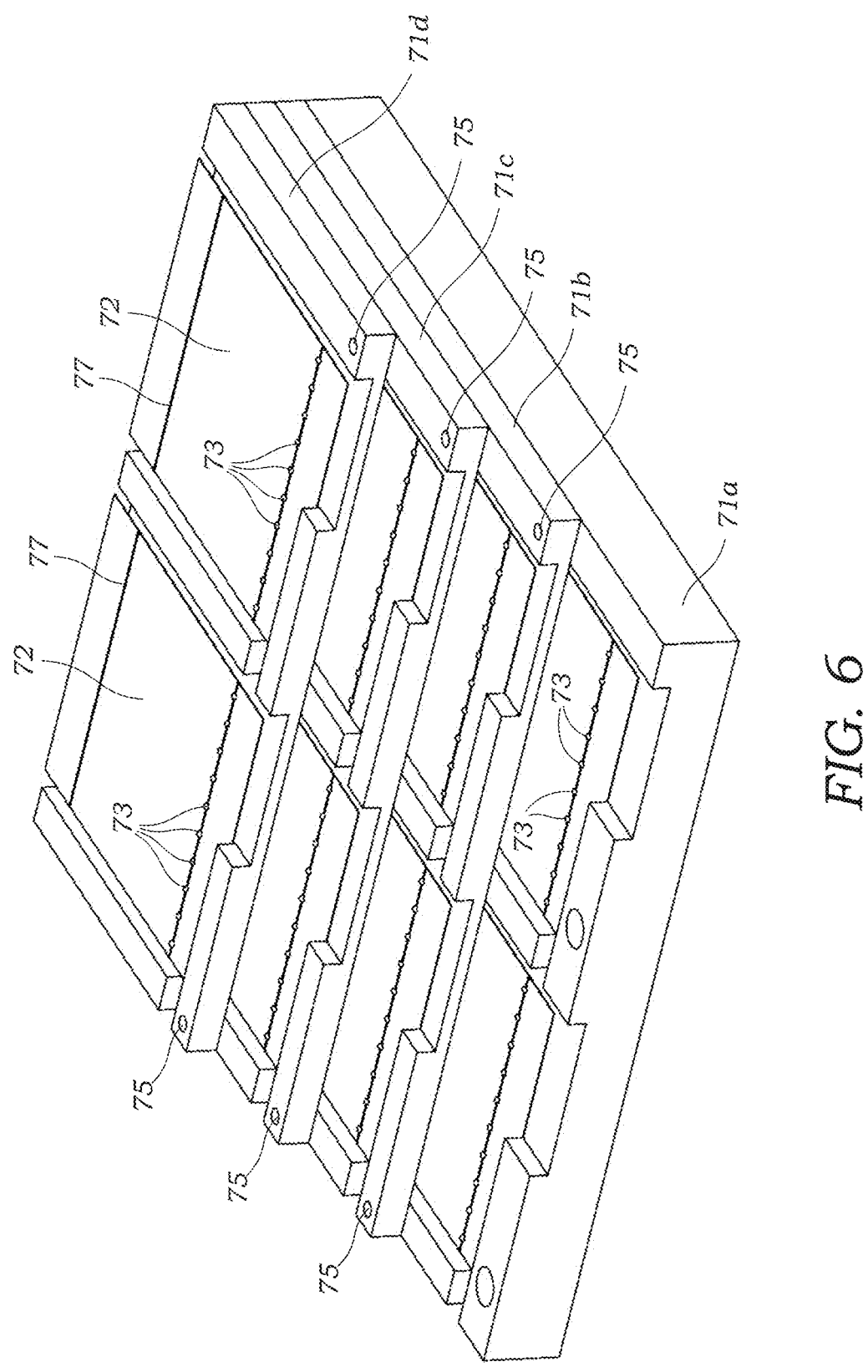
FIG. 6 illustrates a perspective view of a TLC plate holder along with TLC plates (8 TLC plates) loaded therein.

FIG. 6 illustrates a TLC plate holder 70 along with a plurality of TLC plates 72 loaded therein. The TLC plate holder 70 includes a series of stacked layers 71a, 71b, 71c, 71d. The stacked layers 71a, 71b, 71c, 71d are arranged in a staggered or stair-step fashion that permits the nesting of the TLC plates 72 in an offset configuration while still allowing access for the robotic system 60 to access the edges of the TLC plates 72 for spotting. FIG. 6 illustrates how the staggered orientation of the layers still allows access to the spotting locations 73 for each of the TLC plates 72. The marking indicating the final position of the solvent front 77 (for the subsequent development process) is illustrated in two of the TLC plates 72. In this embodiment, there are eight (8) TLC plates 72 held in the holder 70 but other numbers may also be used. The holder 70 may include optional fasteners (e.g., screws, bolts, or the like) that secure the stacked layers 71a, 71b, 71c, 71d and can be removed for loading/unloading of the TLC plates 72. Alternatively, notches provided in the holder 70 around the border of each TLC plate 72 enables one to grab the TLC plates 72 with a tool such as tweezers so that the holder 70 does not need to be disassembled/assembled. The TLC plates 72 can be loaded in a similar manner.

Figure 7:
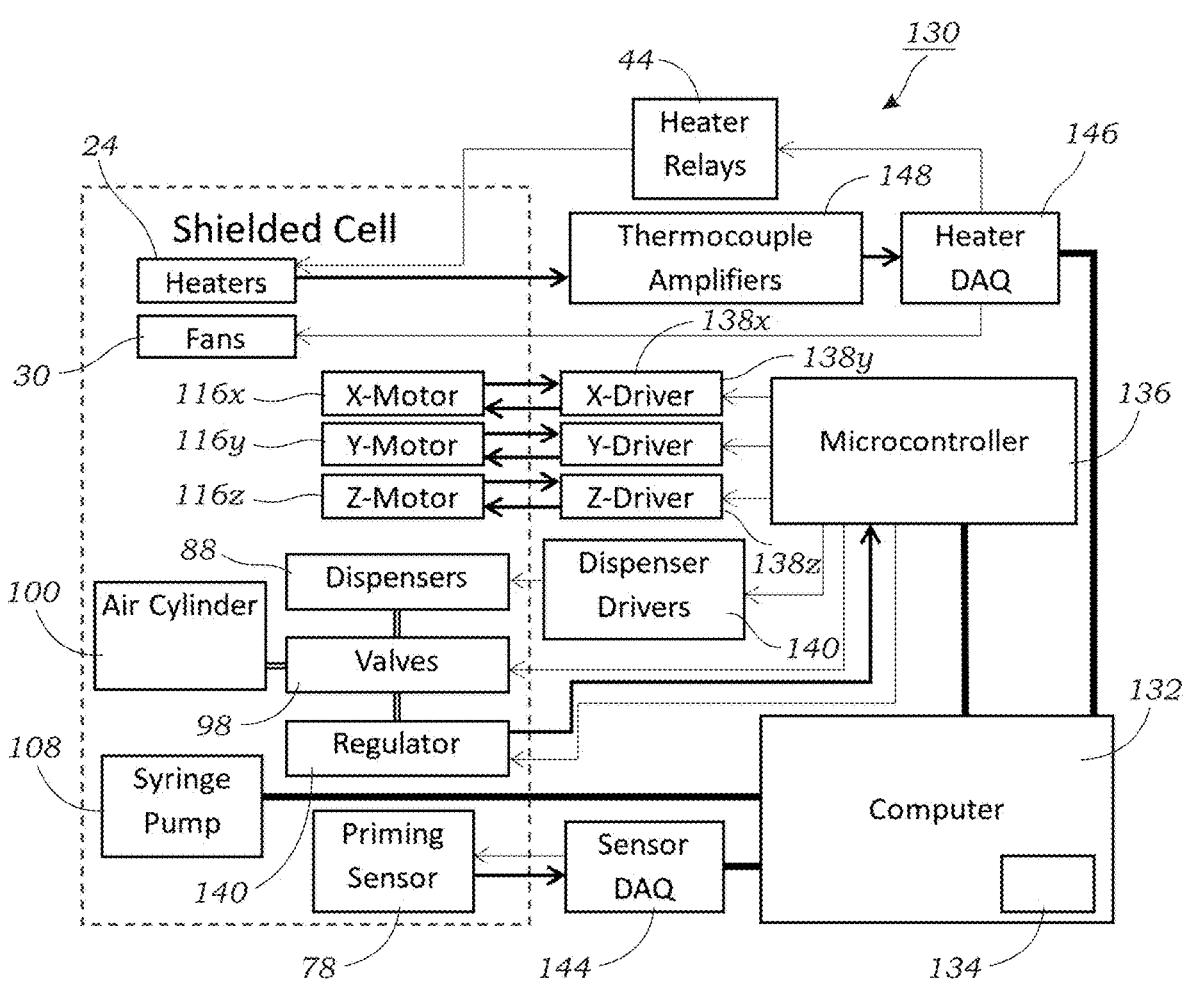
FIG. 7 illustrates a block diagram of the control system used in the automated robotic system for high throughput chemical synthesis. Double lines are air pathways. Thin arrows are digital signals. Thick arrows are analog signals. Thickest lines are communication signals.

FIG. 7 illustrates a schematic of the electronic control system 130 used for the robotic system 60 according to one embodiment. The electronic control system 130 includes a computer 132 that executes software 134 to run the various subsystems (e.g., moveable gantry 84, heaters 24, priming sensor 78, syringe pump 108, dispensers 88). The software 134 may include, for example, the commercially available LabVIEW software program although the invention is not so limited. The software 134 loads a number of configuration files that contain the absolute coordinates of the fixed system components (for the moveable gantry 84), communication protocols including serial command structure, max speed limits for the moveable gantry 84, syringe pump 108 calibration, including maximum volume, speed, and "air-gap" for pipetting, heater 24 calibration profiles and maximum safe temperatures, dispenser 88 liquid profiles, which include calibration details and operating pressure requirements for each dispenser 88, physical geometry definitions of various working areas (microwell plates 66, microfluidic chips or substrates 10, pipette tip rack 68, TLC plate holder 70, etc.,) for use in movement calculations during liquid handling steps, and user-made changes to the system 60, including which plates 66, chips 10, dispenser 88 calibrations, and pipette tips 76 are installed. The software 134 includes a script which includes the list of steps or operations that the robotic system 60 executes. This includes, for example, a list of what components and locations are involved in a particular operation (e.g., particular dispensers 88 and which reaction sites 14 on a microfluidic chip or substrate 10). Programming the software 134 is achieved by writing scripts to implement the various operations and are loaded by the LabVIEW software 134 control program which steps through and performs the programmed list of operations.

It should be appreciated that various software 134 architectures may be used and the actual commands or instructions used to control the various sub-systems may be differently implemented (e.g., different commands, arguments, etc.) The sequence of operations may also be programmed using a graphical user interface (GUI) or the like that allows one to drag-and-drop different unit operations in sequence instead of script files.

Table 1 below lists commands that the system 60 uses to perform a high-throughput experiment. The commands are meant to be broad in scope and experimentally intuitive to allow for many synthesis methods to be performed with this system 60 with a minimum of implementation knowledge required of the operator. For each command, the required inputs as well as a description of its actions in a general sense are included. A "set" notation is used for ease of specifying locations within a given plate or chip when designing a method.

TABLE 1

| Command | Description and Syntax | Parameter | Description |
| --- | --- | --- | --- |
| Transfer_1N_Plate-Chip | Transfer a specified volume from 1 plate well to N different reaction sites on installed chips Transfer_1N_Plate-Chip (SET_FROM_Plate, SET_TO_Chip, VolumeTotal, VolumeEach) | SET_FROM_Plate | Set describing well location to transfer from (P, X, Y) |
| | | SET_TO_Chip | Set describing reaction sites to transfer to (P, X, Y) |
| | | Volume_Total | Total volume required to aspirate from the well |
| | | Volume_Each | Volume to be dispensed to each chip site |
| Transfer_NN_Plate-Chip | Transfer a specified volume from N different plate wells to N different reaction sites on installed chips Transfer_NN_Plate-Chip (SET_FROM_Plate, SET_TO_Chip, VolumeEach, Mix) | SET_FROM_Plate | Set describing well locations to transfer from (P, X, Y) |
| | | SET_TO_Chip | Set describing reaction sites to transfer to (P, X, Y) |
| | | Volume_Each | Volume to be dispensed to each chip site |
| | | Mix | Boolean to define if mixing should occur after each transfer |
| Transfer_1N_Chip-Plate | Transfer a specified volume from 1 different reaction sites on installed chips to N different wells Transfer_1N_Chip-Plate (SET_FROM_Chip, SET_TO_Plate, VolumeTotal, VolumeEach) | SET_FROM_Chip | Set describing reaction sites to transfer from (P, X, Y) |
| | | SET_TO_Plate | Set describing plate wells to transfer to (P, X, Y) |
| | | Volume_Total | Total volume required to aspirate from the reaction site |
| | | Volume_Each | Volume to be dispensed to each chip site |
| Transfer_NN_Chip-Plate | Transfer a specified volume from N different reaction sites on installed chips to N different wells Transfer_NN_Chip-Plate (SET_FROM_Chip, SET_TO_Plate, VolumeEach, Mix) | SET_FROM_Chip | Set describing reaction sites to transfer from (P, X, Y) |
| | | SET_TO_Plate | Set describing plate wells to transfer to (P, X, Y) |
| | | Volume_Each | Volume to be dispensed to each well |
| | | Mix | Boolean to define if mixing should occur after each transfer |
| Dispense_Chip | Dispense a volume of reagent from desired dispenser to reaction sites Dispense_Chip(#Dispenser, SET_TO_Chip, Volume) | #Dispenser | Dispenser variable for this dispense, defined beforehand in method |
| | | SET_TO_Chip | Set describing the reactions sites to dispense reagent to (P, X, Y) |
| | | Volume | Volume to be dispensed to each reaction site (µL) |
| Dispense_Plate | Dispense a volume of reagent from desired dispenser to plate wells Dispense_Plate(#Dispenser, SET_TO_Plate, Volume) | #Dispenser | Dispenser variable for this dispense, defined beforehand in method |
| | | SET_TO_Plate | Set describing the plate wells to dispense reagent to (P, X, Y) |
| | | Volume | Volume to be dispensed to each reaction site (µL) |
| Heat | Sets the array of heaters to the specified temperature for the specified duration Heat([(Temperature, Duration)]) | Array Syntax | ((Temperature1, Duration1), (Temperature2, Duration2) . . .) |
| | | Temperature | Temperature set point for the heater (° C.) |
| | | Duration | Time that the heater should stay at the specified set point (s) |

TABLE 1-continued

| Command | Description and Syntax | | Parameter Description |
|---|---|---|---|
| Heat__Replenish | Sets the array of heaters to the specified temperature for the specified duration, and also dispenses a specific volume to all heaters which have not yet reached their specified duration every interval Heat__Replenish([(Temperature, Time)], #Dispenser, ReplenishTime, (SET__Replenish, Volume)) | Array Syntax | ((Temperature1, Duration1), (Temperature2, Duration2) . . .) |
| | | Temperature | Temperature set point for the heater (° C.) |
| | | Duration | Time that the heater should stay at the specified set point (s) |
| | | #Dispenser | Dispenser variable for this dispense, defined beforehand in method |
| | | ReplenishTime | Interval that must pass between each dispensing to the active chips (s) |
| | | SET__Replenish | Previously defined chip set of all reaction sites that require replenishment. Sites on heaters that have finished their Duration are skipped during dispensing |
| | | Volume | Volume to be dispensed to each reaction site (μL) |
| Plate-TLC | Transfers a small volume from N plate wells to TLC plates which take up one of the other plate locations Plate-TLC (SET__FROM__Plate, SET__TLC, Volume) | SET__FROM__Plate | Set describing well locations to transfer from (P, X, Y) |
| | | SET__TLC | Set describing TLC plate locations to spot to (P, X, Y) |
| | | Volume | Volume to be dispensed to each reaction site (μL) |
| Collect__Chip | Dispenses collection solvent to reaction sites and then transfers that volume to plate wells in series, with multiple repeat dispense/transfers per site Collect__Chip(SET__FROM__Chip, SET__TO__Plate, #Dispenser, Volume__dispense, Volume__initial, N__repeats) | SET__FROM__Chip | Set describing reaction sites to transfer from (P, X, Y) |
| | | SET__TO__Plate | Set describing plate wells to transfer to (P, X, Y) |
| | | #Dispenser | Dispenser variable for this dispense, defined beforehand in method |
| | | Volume__dispense | Volume to dispense each time a transfer happens (μL) |
| | | Volume__initial | Estimated volume expected to be at the reaction sites at the beginning of this action (μL) |
| | | N__repeats | Number of times to repeat the dispense and transfer routine per site |

With reference to FIG. 7, the computer 132 interfaces with a microcontroller 136 (e.g., Arduino Mega although this is just one example). The microcontroller 136 interfaces with motor drivers 138x, 138y, 138z which drive respective motors 116x, 116y, 116z. A standalone motion controller that communicates with the computer 132 may also be used. The microcontroller 136 also interfaces with dispenser drivers 140 which actuate the dispensers 88. The microcontroller 136 is also used to control the valves 98 in the valve manifold 96. The microcontroller 136 also communicates with a gas regulator 140 coupled to the air cylinder 100 which supplied pressurized gas (e.g., nitrogen) to drive fluids as described herein. As seen in FIG. 7, a sensor DAQ module 144 communicates with the computer 132 and interfaces with the priming sensor 78 and is used to detect liquid passing through the priming sensor 78 from either the dispensers 88 or the pipette tip 76 (loaded onto the pipette cone 102). A separate heater DAQ module 146 communicates with the computer 132 and interfaces with thermocouple amplifiers 148 that amplify the signal from the thermocouples within the heaters 24. The heater DAQ module 146 controls the operation of the heaters 24 via heater relays 44 (e.g., similar to FIG. 3 configuration) and cooling device 30 (e.g., fans). As seen in FIG. 7, dashed line A shows the contents of the shielded hot cell or mini-cell 150. That is say, certain components are located inside the hot cell or mini-cell 150 while other components are located external to the hot cell or mini-cell 150.

The pipette/dispenser head 86 in the robotic system is able to move to the different working areas of the device to perform the desired operation. This may include, for example, depositing reagents or other fluids from the dispensers 88 onto the microfluidic chip or substrate 10. Further, the pipette cone 102 may be moved to load a pipette tip 76 which can then be used to a reaction site 14 to transfer the reaction site contents to another working area (e.g., a microwell plate 66 or the TLC plate 72). The pipette cone 102 (with pipette tip 76) may also be used to transfer fluid from the well(s) of the microwell plate 66 to the microfluidic chip or substrate 10 (e.g., precursors, crude product, purified or formulated product or other fluids). Also, for reaction optimizations, it may be preferably to prepare dilution series which are stored in the microwell plate 66 which can then be transferred to the microfluidic chip or substrate 10 using the pipette cone 102 with pipette tip 76.

Figure 8:
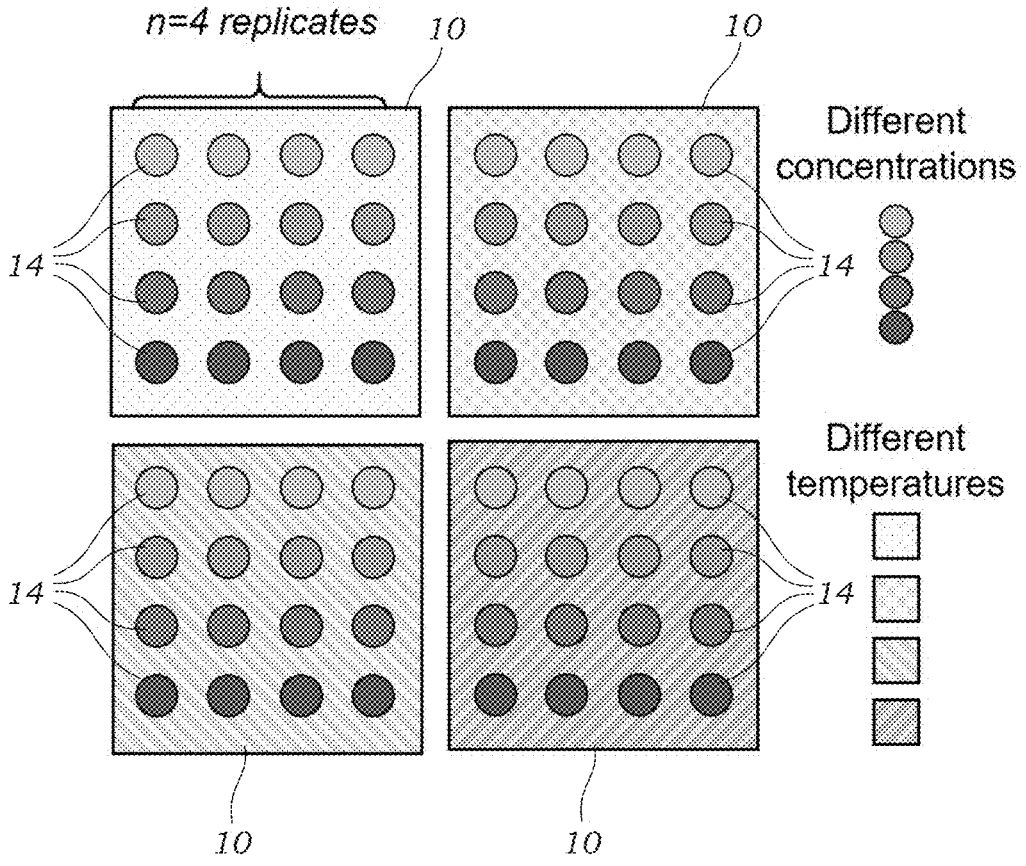
FIG. 8 illustrates an example of how four (4) replicate reaction sites are used to conduct one example of optimization reactions at multiple concentrations. In this example, four (4) precursor concentrations and four (4) different temperatures are explored simultaneously using four (4) microfluidic chips (each microfluidic chip at a different temperature).

As explained herein, the systems 20, 60 described herein may be used to quickly optimize synthesis reactions by enabling multiple reactions to be explored in parallel, each condition with multiple replicates. FIG. 8, for example, illustrates how four (4) replicate reaction sites 14 are used to conduct one example of optimization reactions at multiple concentrations. In this example, four (4) precursor concentrations and four (4) different temperatures are explored simultaneously.

In reaction optimization experiments, in one embodiment, one plate position would contain a pipette tip rack 68 with clean/sterile pipette tips 76, and another plate position for a microwell plate 66 would store the crude product and/or a TLC holder 70 where small samples of the crude product would be deposited. In applications to radiolabel a library of one or more compounds and prepare them for cell assays or injection for imaging, one microwell plate 66 would contain the different compounds/precursors to be labeled, one plate position would contain a pipette tip rack 68 with clean/sterile pipette tips 76, one microwell plate 66 would store the crude products, and one microwell plate 66 would be used to formulate and store the purified crude products. (The purification could be performed for example by ultra-performance liquid chromatography (UPLC)). For both types of applications, all other reagents would be loaded via the non-contact dispensers 88 and stored in reagent vials 92.

In an alternative configuration, various functions may be integrated into a single well plate 66. For example, a fraction of the well plate 66 may contain precursors and another fraction may be empty that can be used to collect crude product from the chip. Other configurations are possible that combine multiple functions onto a single or multiple well plates 66 or similar fluid holders. Custom liquid holders or containers may be used to hold the various reagents, solvents, wash solutions, crude product, etc. The liquid holders or containers may be integrated into one or more cassettes which have the desired volumes needed for the particular synthesis process. This could lead to a more integrated approach where a single custom well plate or cassette could satisfy all needs of the particular experiment or synthesis operation. Such integration could reduce operating costs, improve speed (limiting the amount of distance pipetting robot needs to move), but would reduce flexibility.

The system 20 of FIGS. 2A-2E (with a single heater 24) was used to optimize [$^{18}$F]fallypride production. To control temperature, the microfluidic chip or substrate 10 was placed on a ceramic heater 24 located in the heater platform 22. To test the cross-contamination of adjacent reaction sites on the microfluidic chip 10, an 8 μL droplet of [$^{18}$F]fluoride/TBAHCO$_3$ solution was loaded on one reaction site and 8 μL droplets of TBAHCO$_3$ solution were loaded on the other reaction sites. The chip was heated to 100° C. and radioactivity distribution was assessed via Cerenkov imaging. Next, the droplet-based synthesis of [$^{18}$F]fallypride was performed as seen in FIGS. 9A-9D.

Figures 9A, 9B, 9C, 9D:
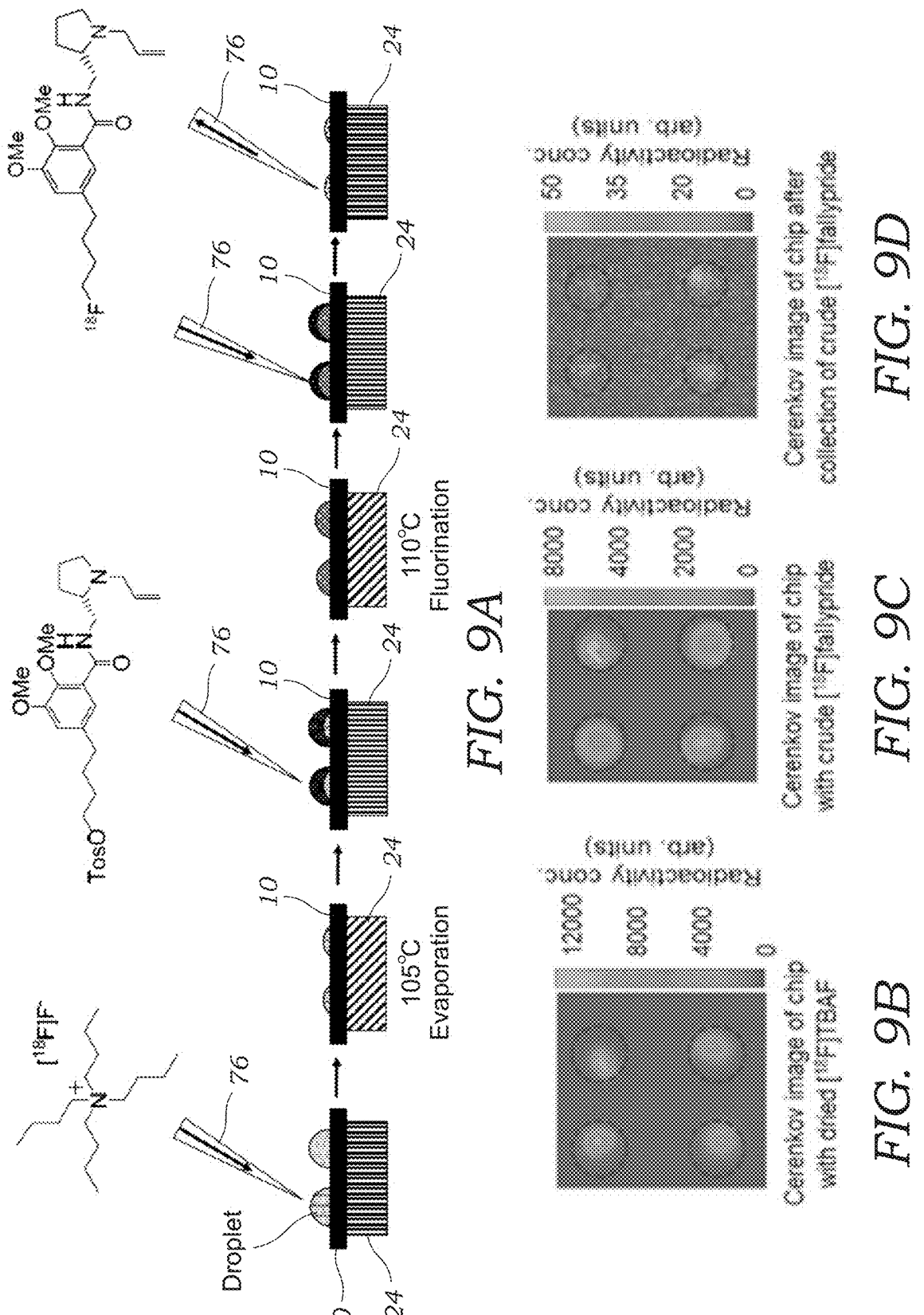
FIG. 9A schematically illustrates the radiochemical synthesis for [$^{18}$F]fallypride using the heater system disclosed herein.
FIG. 9B illustrates a Cerenkov image of the microfluidic chip with dried [$^{18}$F]TBAF.
FIG. 9C illustrates a Cerenkov image of the microfluidic chip with crude [$^{18}$F]fallypride.
FIG. 9D illustrates a Cerenkov image of the microfluidic chip after the collection of crude [$^{18}$F]fallypride.

First, at each site, an 8 μL droplet of [$^{18}$F]fluoride (~3.7 MBq) mixed with TBAHCO$_3$ (240 nmol) was added and then dried at 105° C. for 1 min. Then, a 6 μL droplet of tosyl-fallypride precursor (39 mM) in 1:1 v/v thexyl alcohol/MeCN was added and reacted for 7 min at 110° C. Finally, 20 μL collection solution (90:10 v/v MeOH:water) was loaded on the reaction site 14 to dissolve resulting compounds and the mixed droplet was collected from the microfluidic chip 10. Each reaction site 14 was independently collected for analysis via 3 repeats of the collection process. FIG. 9B is a Cerenkov image showing the distribution of radioactivity on a 2×2 chip (same conditions at all sites) after the evaporation of 8 μL droplets of [$^{18}$F]fluoride mixed with TBAHCO$_3$. FIG. 9C is a Cerenkov image showing the distribution of radioactivity of crude [$^{18}$F] fallypride after the fluorination step. FIG. 9D is a Cerenkov image showing the distribution of the residual radioactivity on the microfluidic chip 10 after collection of the crude [$^{18}$F]fallypride. Brightness is decay-corrected to a common timepoint for all images.

Performance of synthesis was evaluated with dose calibrator and radio thin layer chromatography (radio-TLC; to assess reaction progress) as well as Cerenkov imaging (to assess distribution of radioactivity). When performing synthesis optimization, the droplet synthesis was carried out using multiple sets of conditions to optimize the crude radiochemical yield (RCY). More conditions and/or replicates could be performed in parallel by using chips containing greater number of reaction sites.

Results of the cross-contamination test showed that no radioactivity is transferred from site-to-site during the [$^{18}$F] fluoride drying process. The initial syntheses were performed using the reaction conditions adapted from Wang et al. to gather baseline performance. See Wang et al., Lab Chip, 2017, 17, 4342-4355. The adapted protocol used 30 nmol of TBAHCO$_3$ and a 4 μL droplet of tosyl-fallypride precursor (77 mM). In repeated experiments under identical conditions, high variability of crude RCY was observed from 38-84%, suggesting the reactions were either highly sensitive to certain conditions (e.g. reagent amount) or to a variable that was not accounted for.

The impact of the amount of TBAHCO$_3$ in the reaction was investigated. Standard deviations of data points were small, and the yield showed a clear dependence on the amount of base. From nearly zero yield at low base amount, the yield sharply rises to ~86% at ~80 nmol of base, where it remains relatively stable, and then falls off again with higher base amounts. The highest yield (92±1%, n=2) was obtained at 240 nmol. The very high sensitivity to base at 30 nmol may suggest why high variability was observed under the original synthesis conditions: a small variation in the amount of base (e.g. due to pipetting error when adding the [$^{18}$F]fluoride/TBAHCO$_3$ solution) could result in large variation in yield. The relatively low slope in the 80-240 nmol range suggests the yield would be fairly immune to pipetting errors.

The effect of fluorination reaction volume on yield was evaluated, using 240 nmol of TBAHCO$_3$ in the initial [$^{18}$F]fluoride/TBAHCO$_3$ droplet and 77 mM concentration of precursor solution. The crude RCY yield showed a strong dependence on reaction volume, rising from a moderate value (43±3%, n=4) for a 2 μL reaction to nearly 100% for volumes of 4, 6, and 8 μL. Based on visual observations, it was suspected that the smaller volumes are not sufficient to fully wet the reaction site and thus some of the dried [$^{18}$F]TBAF residue remaining after the drying step does not get dissolved into the reaction droplet. A reaction volume of 6 μL was chosen for subsequent experiments as in that region the flat slope of the graph indicates an insensitivity to errors in precursor droplet volume.

Figures 10A, 10B, 10C:
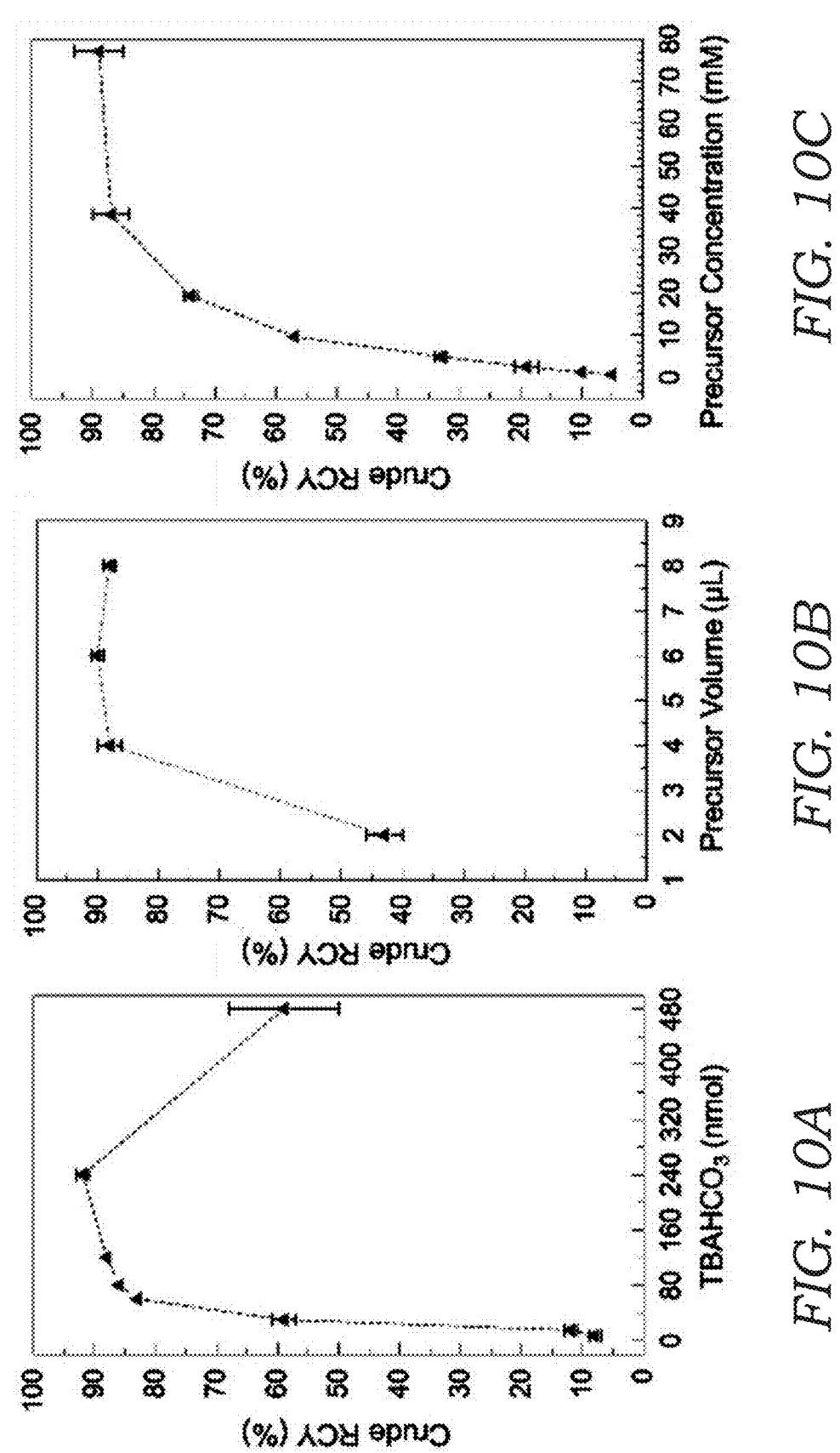
FIG. 10A shows a graph of crude RCY (%) of [$^{18}$F] Fallypride as a function of TBAHCO$_3$ concentration showing the effect of concentration of base solution.
FIG. 10B shows a graph of crude RCY (%) of [$^{18}$F] Fallypride as a function of precursor volume showing the effect of volume of precursor solution.
FIG. 10C shows a graph of crude RCY (%) of [$^{18}$F] Fallypride as a function of precursor concentration showing the effect of concentration of the precursor solution.

Finally, the influence of precursor concentration was explored, when using 240 nmol of TBAHCO$_3$ and a 6 μL fluorination reaction volume. Crude RCY was near zero for low precursor concentrations, increasing rapidly with precursor concentration, and reaching a plateau with near 100% yield above ~40 mM. At the optimal conditions (240 nmol TBAHCO$_3$, 6 μL reaction volume, and 39 mM precursor concentration), the fluorination efficiency was 96.0±0.5% (n=2) and crude RCY was 87±3% (n=2). FIGS. 10A-10C illustrate the FIGS. 10A-10C illustrate the influence of reaction parameters on the performance of the microdroplet synthesis of [$^{18}$F]Fallypride, explored using the high-throughput platform. FIG. 10A shows the effect of concentration of base solution. Reaction volume: 4 μL. Precursor solution concentration: 77 mM. The optimal value was taken as 240 nmol of $TBAHCO_3$, with crude RCY of 92±1% (n=2). FIG. 10B shows the effect of volume of precursor solution. Base amount: 240 nmol. Precursor solution concentration: 77 mM. The optimal value was taken as 6 μL, with crude RCY of 90±1% (n=4). FIG. 10C shows the effect of concentration of the precursor solution. Base amount: 240 nmol. Precursor solution volume: 6 μL. The optimal value was taken as 39 mM, with crude RCY of 87±3% (n=2). The optimized reaction conditions found using the multi-reaction microdroplet chip 10 provided higher and more consistent crude RCY compared to previous reports using microscale platforms.

Cerenkov imaging revealed an absence of cross-contamination even at the 4×4 configuration and the closer spacing between adjacent reaction sites 14. The performance of radiochemistry processes and reactions exhibited high consistency among reaction sites 14 on the high-throughput microfluidic chip 10. This suggests that the platform can be used to quickly optimize reactions (e.g., synthesis of [$^{18}$F] fallypride or other radiochemicals) by enabling multiple reaction conditions to be explored in parallel, each condition with multiple replicates. In addition, multiple parameters such as $TBAHCO_3$ and precursor concentrations were tested within a single day. While sixteen (16) conditions were demonstrated here, the platform could be further scaled by increasing the number of reactions per microfluidic chip 10 or the number of heaters 24. For example, a multi-heater 24 embodiment may be used to perform reactions at different temperatures or at the same temperature but with different heating times. In addition, the design of the microfluidic chip or substrate 10 enables one to easily modify concentrations, solvents, volumes, etc. from reaction site 14 to reaction site 14.

For example, the synthesis of [$^{18}$F]fallypride was optimized as a function of $TBAHCO_3$ and precursor concentrations in a single day for a system 20 that used four (4) heaters 24 as illustrated in FIGS. 2A-2E. Under optimized conditions, fluorination efficiencies up to 99±0% (n=2) and crude radiochemical yield (RCY) up to 92±3% (n=2) was observed. Table 2 below shows the collection efficiency, fluorination efficiency, and crude RCY of [$^{18}$F]fallypride as a function of $TBAHCO_3$ concentration. All conditions n=2.

TABLE 2

| [$TBAHCO_3$] (mM) | Collection Efficiency (%) | Fluorination Efficiency (%) | Crude RCY (%) |
|---|---|---|---|
| 60 | 94 ± 1 | 63 ± 11 | 59 ± 9 |
| 30 | 94 ± 1 | 99 ± 0 | 92 ± 1 |

TABLE 2-continued

| [$TBAHCO_3$] (mM) | Collection Efficiency (%) | Fluorination Efficiency (%) | Crude RCY (%) |
|---|---|---|---|
| 15 | 93 ± 1 | 96 ± 1 | 88 ± 0 |
| 10 | 92 ± 1 | 94 ± 1 | 86 ± 0 |
| 7.5 | 91 ± 3 | 92 ± 2 | 83 ± 0 |
| 3.75 | 90 ± 0 | 65 ± 2 | 59 ± 2 |
| 1.88 | 91 ± 2 | 13 ± 1 | 12 ± 1 |
| 0.9 | 88 ± 1 | 9 ± 1 | 8 ± 1 |

Table 3 below shows the collection efficiency, fluorination efficiency, and crude RCY of [$^{18}$F]fallypride as a function of precursor concentration. All conditions n=2.

TABLE 3

| [Precursor] (mM) | Collection Efficiency (%) | Fluorination Efficiency (%) | Crude RCY (%) |
|---|---|---|---|
| 77 | 92 ± 2 | 97 ± 2 | 89 ± 4 |
| 38.5 | 91 ± 2 | 96 ± 0 | 87 ± 3 |
| 19.25 | 91 ± 0 | 81 ± 0 | 74 ± 1 |
| 9.6 | 91 ± 1 | 63 ± 1 | 53 ± 0 |
| 4.8 | 89 ± 1 | 37 ± 1 | 33 ± 1 |
| 2.4 | 89 ± 2 | 22 ± 2 | 19 ± 2 |
| 1.2 | 82 ± 1 | 13 ± 1 | 10 ± 0 |
| 0.9 | 82 ± 4 | 7 ± 1 | 5 ± 0 |

Figures 11A, 11B, 11C:
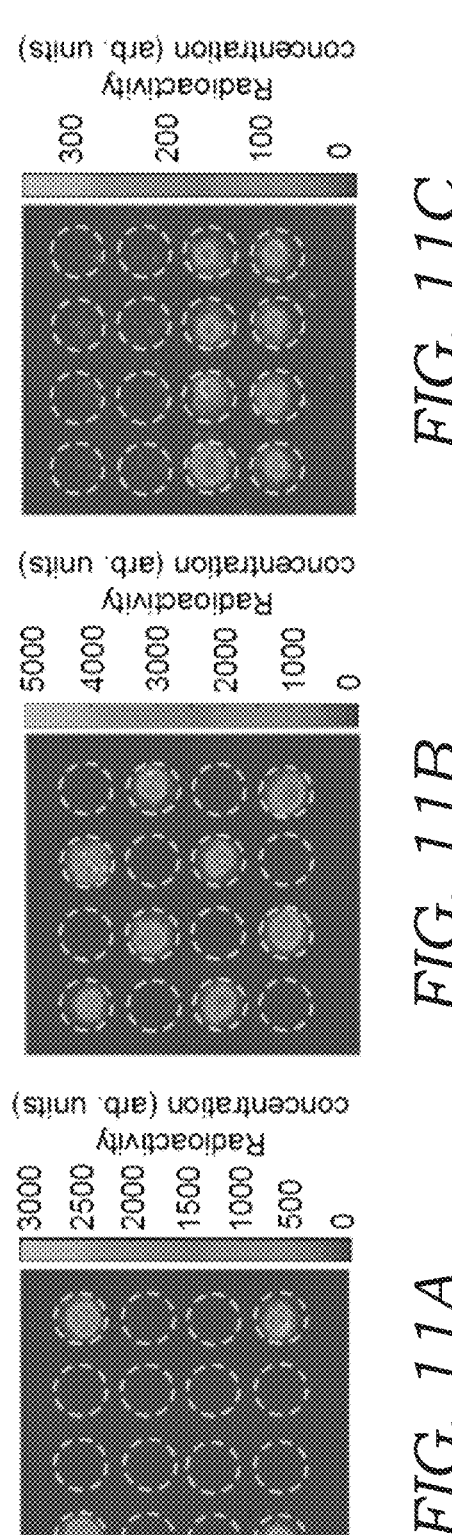
FIGS. 11A-11C illustrate cross-contamination and repeatability tests using 4×4 chips.

FIGS. 11A-11C illustrates the testing results of cross-contamination on 4×4 microfluidic chips 10 (with sixteen reaction sites 14) to see if the closer spacing had an impact on cross-contamination. One pattern was made by loading an 8 μL droplet of [$^{18}$F]fluoride solution (~3.6 MBq) on the reaction sites 14 at the four corners of the 4×4 array, and another pattern was made by loading an 8 μL droplet of [$^{18}$F]fluoride solution on alternating reaction sites 14. The remaining reaction sites 14 were each filled with an 8 μL droplet of DI water. Then, the microfluidic chips 10 were dried at 100° C. for 1 min, followed by CLI imaging (FIGS. 9A-9C). To assess the repeatability on the 4×4 chip, 8 μL of two different concentrations of [$^{18}$F]fluoride/$TBAHCO_3$ solution were loaded onto the microfluidic chip 10: ~3.6 MBq [$^{18}$F]fluoride and 30 mM [240 nmol] $TBAHCO_3$ in the first 2 rows and ~3.6 MBq [$^{18}$F]fluoride and 0.9 mM [7 nmol] $TBAHCO_3$ in the second two rows. After the drying step was performed, 6 μL of 39 mM precursor was added to all reaction sites 14 and the fluorination reaction was performed by heating the entire microfluidic chip 10. The crude products were collected and analyzed (Table 4) and a CLI image of the chip after sample collection was obtained (FIG. 11C).

TABLE 4

| | Performance measure | Column 1 | Column 2 | Column 3 | Column 4 | Average ± std dev (n = 4) |
|---|---|---|---|---|---|---|
| Row 1 | Collection efficiency (%) | 93 | 92 | 94 | 94 | 93 ± 1 |
| | Fluorination efficiency (%) | 93 | 92 | 93 | 90 | 92 ± 1 |
| | Crude RCY (%) | 87 | 84 | 87 | 84 | 86 ± 2 |
| Row 2 | Collection efficiency (%) | 92 | 95 | 92 | 93 | 93 ± 2 |
| | Fluorination efficiency (%) | 89 | 91 | 91 | 89 | 90 ± 1 |
| | Crude RCY (%) | 81 | 86 | 84 | 83 | 84 ± 2 |
| Row 3 | Collection efficiency (%) | 92 | 84 | 89 | 88 | 89 ± 3 |
| | Fluorination efficiency (%) | 50 | 41 | 41 | 40 | 43 ± 5 |
| | Crude RCY (%) | 46 | 35 | 36 | 35 | 38 ± 5 |
| Row 4 | Collection efficiency (%) | 91 | 86 | 88 | 95 | 90 ± 4 |
| | Fluorination efficiency (%) | 41 | 45 | 39 | 44 | 42 ± 3 |
| | Crude RCY (%) | 37 | 39 | 34 | 42 | 38 ± 3 |

Table 4 shows the synthesis performance from sixteen (16) sites on a 4×4 microfluidic chip 10 using two different base concentrations (n=8 each) corresponding to FIG. 11C. For all reactions, precursor concentration was 39 mM, and volume of precursor solution was 6 μL. TBAHCO₃ amount was 240 nmol in the reactions of rows 1 and 2 on the chip, and 7 nmol in rows 3 and 4. High reproducibility is evident. The higher variability in rows 3 and 4 may be caused by the higher sensitivity to salt concentration under this condition. It should be appreciated that a wide variety of radiochemicals may be synthesized using the systems 20, 60. These include by way of illustration and not limitation, [18F] Fallypride and [18F]Flumazenil, [18F]FDOPA, [18F]FET, [18F]Florbetaben, and [18F]PBR06.

In one embodiment, a chromatographic separation unit (e.g., a HPLC or UPLC unit) may be integrated into the robotic system 60. The UPLC may be used for analyzing reaction products for optimization studies, or for purification of compounds, that would be followed by formulation into a directly injectable PET tracer. The latter may also include a preconditioned high-throughput solid-phase extraction plate and sterile filter plate to formulate multiple samples in parallel (trap, wash, elute, dilute with saline). The resulting compounds are then ready for preclinical injection. The robotic system 60 may also be integrated with one or more of a dose calibrator, gamma counter, gas chromatography mass spectrometer (GC-MS), liquid chromatography mass spectrometer (LC-MS). The radiochemical product is subject to further processing and/or analysis using these units/ devices.

To use the systems 20, 60, one or more microfluidic chips or substrates 10 are disposed atop the one or more heaters 24. The reaction sites 14 are then loaded with appropriate fluid reagents used for the particular synthesis operation. The reaction sites 14 may be loaded manually or, alternatively, using the robotic system 60 as described herein. The microfluidic chip or substrates 10 are subject to heating and/or cooling using the one or more heaters 24 and cooling device(s) 30. Intermediate or final reaction products can be removed from the reaction sites 14 using a pipette or the like which again may be a manual operation or automated using the robotic system 60. In one embodiment, the reaction products may be loaded onto one or more TLC plates 72 such as that described herein. In addition, the reaction products may also be subject to purification and/or formulation using, for example, UPLC or the like.

While embodiments of the present invention have been shown and described, various modifications may be made without departing from the scope of the present invention. For example, the moveable gantry 88 illustrated herein uses a carriage/rail system to move in the x, y, and z direction. Different robotic actuation schemes may also be employed to move the pipette/dispenser head 86 in the x, y, and z directions for fluid dispensing/retrieval. For example, a Selective Compliance Articulated Robot Arm (SCARA) may be used in combination with a z-adjust assembly (e.g. z carriage and motor) may also be used to move the moveable gantry 88. Other robotic schemes may also be used to move the moveable gantry 88 in the x, y, and z directions. The invention, therefore, should not be limited, except to the following claims, and their equivalents.

What is claimed is:

1. A high throughput radiochemistry system comprising:
a frame including a base plate;
a heater platform disposed on the base plate and containing a plurality of heaters therein and defining a flat upper surface configured to hold a plurality of microfluidic chips or substrates thereon, wherein the plurality of microfluidic chips or substrates have a plurality of reaction sites formed thereon, the heater platform containing a plurality of controllable heaters each coupled to heater control circuitry;
one or more cooling devices in thermal contact with the heater platform;
a robotic system for reagent dispensing and product collecting/sampling, the robotic system comprising a robotic moveable gantry configured to move in the x, y, and z direction and having a head secured to the moveable gantry, the head having a plurality of dispensers and a pipette cone disposed therein, wherein the pipette cone is secured to an actuator via a bracket and configured to move the pipette cone in the z direction independent of the robotic moveable gantry;
a controller programed to manipulate the moveable gantry, the plurality of dispensers, and actuator; and
one or more microwell storage areas and at least one or more pipette tip racks disposed in respective nests disposed on the base plate.

2. The system of claim 1, wherein the heater control circuitry comprises a temperature sensor associated with each of the plurality of heaters and respective relays.

3. The system of claim 1, wherein the actuator comprises a pneumatic actuator.

4. The system of claim 1, wherein the one or more cooling devices comprises one or more of: a fan, a heat sink, a heat pipe, a liquid cooler, evaporative cooler, and a thermoelectric cooler.

5. The system of 1, further comprising a priming sensor, the priming sensor comprising a notch or partial opening and a light beam emitter and receiver disposed across the notch or partial opening.

6. The system of claim 1, wherein the system comprises a base plate containing a nest for holding one or more TLC plate holders.

7. The system of claim 6, wherein each of the TLC plate holders comprises a plurality of TLC plates stacked in a staggered configuration.

8. The system of claim 1, further comprising a pipette removal fork disposed on the base plate.

9. The system of claim 1, wherein the heater platform comprises a ceramic holder having the plurality of heaters potted in the ceramic holder.

10. The system of claim 1, wherein the heater platform comprises at least four heaters.

11. The system of claim 1, further comprising a chromatography system for analysis or purification of radiochemicals obtained from the reaction sites.

12. The system of claim 1, the frame further comprising a top, sides, and back braces.

13. The system of claim 1, wherein the plurality of dispensers comprise non-contact dispensers.

14. The system of claim 1, wherein the heater platform is supported on the base plate by a plurality of stands and wherein the one or more cooling devices comprise respective fans disposed beneath the plurality of heaters.

15. The system of claim 14, wherein the respective fans are mounted to a base secured to the heater platform, wherein the base further comprises a plurality of exhaust vents.

* * * * *